(12) United States Patent
Burde et al.

(10) Patent No.: US 7,385,049 B2
(45) Date of Patent: Jun. 10, 2008

(54) OLIGONUCLEOTIDES AND METHODS FOR DETECTION OF WEST NILE VIRUS

(75) Inventors: Stefan H. M. Burde, Cary, NC (US); Todd M. Gierman, Cary, NC (US); Christopher C. Glenn, Holly Springs, NC (US)

(73) Assignee: Bayer HealthCare LLC, Tarytown, NY (US)

( * ) Notice: Subject to any disclaimer, the term of this patent is extended or adjusted under 35 U.S.C. 154(b) by 314 days.

(21) Appl. No.: 10/985,805

(22) Filed: Nov. 10, 2004

(65) Prior Publication Data

US 2005/0130133 A1 Jun. 16, 2005

Related U.S. Application Data

(60) Provisional application No. 60/519,096, filed on Nov. 12, 2003.

(51) Int. Cl.
C07H 21/04 (2006.01)
(52) U.S. Cl. .......................... 536/24.3; 435/5; 435/34; 435/339
(58) Field of Classification Search .................... None
See application file for complete search history.

(56) References Cited

U.S. PATENT DOCUMENTS 6,214,979 B1 * 4/2001 Gelfand et al. ............ 536/22.1
2005/0164170 A1 7/2005 Despres et al.

FOREIGN PATENT DOCUMENTS

RU 2199589 2/2003

OTHER PUBLICATIONS

AF404756, Ebel et al., 2002, p. 1-6.*
AF206518, Anderson et al., 1999, p. 1-6.*
AF458350, Beasley et al., 2002, p. 1-2.*
AF458351, Beasley et al., 2002, p. 1-2.*
"Detection of West Nile Virus in Blood Donations United States, 2003"; Morbidity and Mortality Weekly Report 52(32): 769-772 (Aug. 15, 2003).
Anderson, J.F. et al., "A Phylogenetic approach to following West Nile virus in Connecticut"; PNAS, Nov. 6, 2001, vol. 98, No. 23 12885-12889.
Anderson, J.F. et al., "Isolation of West Nile Virus from Mosquitoes, Crows, and a Cooper's Hawk in Connecticut", SCIENCE, vol. 286, pp. 2331-2333; Dec. 17, 1999.
Briese, T. et al., "Phylogeneic Analusis of a Human Isolate from the 2000 Israel West Nile virus Epidemic"; Emerging Infectious Diseases, vol. 8, No. 5, May 2002.
Burt, F.J. et al., "Swanepoel, Robert; Phylognetic Relationships of Southern African West Nile Virus Isolates", Emerging Infectious Diseases, vol. 8, No. 8, Aug. 2002.
Garmendia, A.E. et al., "Recovery and Identification of West Nile Virus from a Hawk in Winter"; Journal of Clinical Microbiology, vol. 38, No. 8, pp. 3110-3111; Aug. 2000.
Huang, C. et al., First isolation of West Nile Virus from a Patient with Encepheiitis in the United States . Emerging Infectious Diseases, vol 8. No. 12, Dec. 2002.
Jia, X. et al., "Genetic Analysis of West Nile New York 1999 Encephalitis Virus", The Lancet, vol. 354, pp. 1971-1972, Dec. 4, 1999.
Johnson, D. et al., "Detection of North American West Nile Virus in Animal Tissue by a Reverse Transcription Nested Polymerase Chain Reaction Assay"; Emerging Infectious Diseases, vol. 7, No. 4, Jul.-Aug. 2001.
Lanciotti, R.G. et al., "Rapid Detection of West Nile Virus from Human Clinical Specimens, Field-Collected Mosquitoes, and Avian Samples by a TaqMan Reverse Transcriptase-PCR Assay"; Journal of Clincial Microbiology, vol. 38, No. 11, pp. 4066-1071, Nov. 2000.
Lanciotti, R.S. et al., "Complete Genome Sequence and Phylogenetic Analysis of West Nile Virus Strains Isolated from the United States, Europe, and the Middle East"; Virology, vol. 298, pp. 96-105 (2002).
Lanciotti, R.S. et al., "Origin of the West Nile Virus Responsible for an Outbreak of Encephalitis in the Northeastern United States"; Science, vol. 286, Dec. 17, 1999.
Platonov, A.E. et al., "Outbreak of West Nile Virus Infection, Volgograd Region, Russia, 1999"; Emerging Infectious Diseases, vol. 7, No. 1, Jan.-Feb. 2001.
Scaramozzino, N. et al., "Comparison of *Flavivirus* Universal Primer Pairs and Development of a Rapid, Highly Sensitive, Heminested Reverse Transcription-PCR Assay for Detection of Flaviviruses Targeted to a Conserved Region of the NS5 Gene Sequences"; Journal of Clincial Microbiology, vol. 39, No. 5, pp. 1922-1927, May 2001.
Shi, P. et al., "High-throughput Detection of West Nile Virus RNA", Journal of Clinical Microbiology, vol. 39, No. 4, pp. 1264-1271, Apr. 2001.
Steele, K.E. et al., "Pathology of Fatal West Nile Virus Infections in Native and Exotic Birds during the 1999 Outbreak in New York City, New York"; Vet Pathol 37; 208-224 (2000).
GenBank Accession No. AF 196835 West Nile Virus, 1999.
GenBank Accession No. AF 260967, West Nile Virus, 2000.
GenBank Accession No. AF 202541, West Nile Virus, 1999.
GenBank Accession No. AF 206518, West Nile Virus, 1999.
GenBank Accession No. AF 404753, West Nile Virus, 2002.
GenBank Accession No. AF 404754, West Nile Virus, 2002.
GenBank Accession No. AF 404755, West Nile Virus, 2002.
GenBank Accession No. AF 404756, West Nile Virus, 2002.
GenBank Accession No. AY033389, West Nile Virus, 2002.

* cited by examiner

*Primary Examiner*—Bruce R. Campell
*Assistant Examiner*—Agnieszka Boesen
(74) *Attorney, Agent, or Firm*—Connolly Bove Lodge & Hutz LLP

(57) ABSTRACT

The invention provides methods of detecting West Nile virus and oligonucleotide reagents derived from a West Nile virus consensus sequence that are useful in the methods of the invention.

24 Claims, 3 Drawing Sheets

FIG. 1A U.S. Strain West Nile Virus Consensus Sequence

5'-
AGTAGTTCGCCTGTGTGAGCTGACAAACTTAGTAGTGTTTGTGAGGATTAACAACAATTAACACAGTGCGAGCTGTT
TCTTAGCACGAAGATCTCGATGTCTAAGAAACCAGGAGGGCCCGGCAAGAGCCGGGCTGTCAATATGCTAAAACGCG
GAATGCCCCGCGTGTTGTCCTTGATTGGACTGAAGAGGGCTATGTTGAGCCTGATCGACGGCAAGGGGCCAATACGA
TTTGTGTTGGCTCTCTTGGCGTTCTTCAGGTTCACAGCAATTGCTCCGACCCGAGCAGTGCTGGATCGATGGAGAGG
TGTGAACAAACAAACAGCGATGAAACACCTTCTGAGTTTTAAGAAGGAACTAGGGACCTTGACCAGTGCTATCAATC
GGCGGAGCTCAAAACAAAAGAAAAGAGGAGGAAAGACCGGAATTGCAGTCATGATTGGCCTGATCGCCAGCGTAGGA
GCAGTTACCCTCTCTAACTTCCAAGGGAAGGTGATGATGACGGTAAATGCTACTGACGTCACAGATGTCATCACGAT
TCCAACAGCTGCTGGAAAGAACCTATGCATTGTCAGAGCAATGGATGTGGGATACATGTGCGATGATACTATCACTT
ATGAATGCCCAGTGCTGTCGGCTGGTAATGATCCAGAAGACATCGACTGTTGGTGCACAAAGTCAGCAGTCTACGTC
AGGTATGGAAGATGCACCAAGACACGCCACTCAAGACGCAGTCGGAGGTCACTGACAGTGCAGACACACGGAGAAAG
CACTCTAGCGAACAAGAAGGGGGCTTGGATGGACAGCACCAAGGCCACAAGGTATTTGGTAAAAACAGAATCATCGA
TCTTGAGGAACCCTGGATATGCCCTGGTGGCAGCCGTCATTGGTTGGATGCTTGGGAGCAACACCATGCAGAGAGTT
GTGTTTGTCGTGCTATTGCTTTTGGTGGCCCCAGCTTACAGCTTCAACTGCCTTGGAATGAGCAACAGAGACTTCTT
GGAAGGAGTGTCTGGAGCAACATGGGTGGATTTGGTTCTCGAAGGCGACAGCTGCGTGACTATCATGTCTAAGGACA
AGCCTACCATCGATGTGAAGATGATGAATATGGAGGCGGCCAACCTGGCAGAGGTCCGCAGTTATTGCTATTTGGCT
ACCGTCAGCGATCTCTCCACCAAAGCTGCGTGCCCGACCATGGGAGAAGCTCACAATGACAAACGTGCTGACCCAGC
TTTTGTGTGCAGACAAGGAGTGGTGGACAGGGGCTGGGGCAACGGCTGCGGACTATTTGGCAAAGGAAGCATTGACA
CATGCGCCAAATTTGCCTGCTCTACCAAGGCAATAGGAAGAACCATCTTGAAAGAGAATATCAAGTACGAAGTGGCC
ATTTTTGTCCATGGACCAACTACTGTGGAGTCGCACGGAAACTACTCCACACAGGTTGGAGCCACTCAGGCAGGGAG
ATTCAGCATCACTCCTGCGGCGCCTTCATACACACTAAAGCTTGGAGAATATGGAGAGGTGACAGTGGACTGTGAAC
CACGGTCAGGGATTGACACCAATGCATACTACGTGATGACTGTTGGAACAAAGACGTTCTTGGTCCATCGTGAGTGG
TTCATGGACCTCAACCTCCCTTGGAGCAGTGCTGGAAGTACTGTGTGGAGGAACAGAGAGACGTTAATGGAGTTTGA
GGAACCACACGCCACGAAGCAGTCTGTGATAGCATTGGGCTCACAAGAGGGAGCTCTGCATCAAGCTTTGGCTGGAG
CCATTCCTGTGGAATTTTCAAGCAACACTGTCAAGTTGACGTCGGGTCATTTGAAGTGTAGAGTGAAGATGGAAAAA
TTGCAGTTGAAGGGAACAACCTATGGCGTCTGTTCAAAGGCTTTCAAGTTTCTTGGGACTCCCGCAGACACAGGTCA
CGGCACTGTGGTGTTGGAATTGCAGTACACTGGCACGGATGGACCTTGCAAAGTTCCTATCTCGTCAGTGGCTTCAT
TGAACGACCTAACGCCAGTGGGCAGATTGGTCACTGTCAACCCTTTTGTTTCAGTGGCCACGGCCAACGCTAAGGTC
CTGATTGAATTGGAACCACCCTTTGGAGACTCATACATAGTGGTGGGCAGAGGAGAACAACAGATCAATCACCATTG
GCACAAGTCTGGAAGCAGCATTGGCAAAGCCTTTACAACCACCCTCAAAGGAGCGCAGAGACTAGCCGCTCTAGGAG
ACACAGCTTGGGACTTTGGATCAGTTGGAGGGGTGTTCACCTCAGTTGGGAAGGCTGTCCATCAAGTGTTCGGAGGA
GCATTCCGCTCACTGTTCGGAGGCATGTCCTGGATAACGCAAGGATTGCTGGGGGCTCTCCTGTTGTGGATGGGCAT
CAATGCTCGTGATAGGTCCATAGCTCTCACGTTTCTCGCAGTTGGAGGAGTTCTGCTCTTCCTCTCCGTGAACGTGC
ACGCTGACACTGGGTGTGCCATAGACATCAGCCGGCAAGAGCTGAGATGTGGAAGTGGAGTGTTCATACACAATGAT
GTGGAGGCTTGGATGGACCGGTACAAGTATTACCCTGAAACGCCACAAGGCCTAGCCAAGATCATTCAGAAAGCTCA
TAAGGAAGGAGTGTGCGGTCTACGATCAGTTTCCAGACTGGAGCATCAAATGTGGGAAGCAGTGAAGGACGAGCTGA
ACACTCTTTTGAAGGAGAATGGTGTGGACCTTAGTGTCGTGGTTGAGAAACAGGAGGGAATGTACAAGTCAGCACCT
AAACGCCTCACCGCCACCACGGAAAAATTGGAAATTGGCTGGAAGGCCTGGGGAAAGAGTATTTTATTTGCACCAGA
ACTCGCCAACAACACCTTTGTGGTTGATGGTCCGGAGACCAAGGAATGTCCGACTCAGAATCGCGCTTGGAATAGCT
TAGAAGTGGAGGATTTTGGATTTGGTCTCACCAGCACTCGGATGTTCCTGAAGGTCAGAGAGAGCAACACAACTGAA
TGTGACTCGAAGATCATTGGAACGGCTGTCAAGAACAACTTGGCGATCCACAGTGACCTGTCCTATTGGATTGAAAG
CAGGCTCAATGATACGTGGAAGCTTGAAAGGGCAGTTCTGGGTGAAGTCAAATCATGTACGTGGCCTGAGACGCATA
CCTTGTGGGGCGATGGAATCCTTGAGAGTGACTTGATAATACCAGTGCACACTGGCGGGACCACGAAGCAATCACAAT
CGGAGACCTGGGTACAAGCACAAAACCAGGGCCCATGGGACGAAGGCCGGGTAGAGATTGACTTCGATTACTGCCC
AGGAACTACGGTCACCCTGAGTGAGAGCTGCGGACACCGTGGACCTGCCACTCGCACCACCACAGAGAGCGGAAAGT
TGATAACAGATTGGTGCTGCAGGAGCTGCACCTTACCACCACTGCGCTACCAAACTGACAGCGGCTGTTGGTATGGT
ATGGAGATCAGACCACAGAGACATGATGAAAAGACCCTCGTGCAGTCACAAGTGAATGCTTATAATGCTGATATGAT
TGACCCTTTTCAGTTGGGCCTTCTGGTCGTGTTCTTGGCCACCCAGGAGGTCCTTCGCAAGAGGTGGACAGCCAAGA
TCAGCATGCCAGCTATACTGATTGCTCTGCTAGTCCTGGTGTTTGGGGCATTACTTACACTGATGTGTTACGCTAT
GTCATCTTGGTGGGGGCAGCTTTCGCAGAATCTAATTCGGGAGGAGACGTGGTACACTTGGCGCTCATGGCGACCTT

FIG. 1B

```
CAAGATACAACCAGTGTTTATGGTGGCATCGTTTCTCAAAGCGAGATGGACCAACCAGGAGAACATTTTGTTGATGT
TGGCGGCTGTTTTCTTTCAAATGGCTTATCACGATGCCCGCCAAATTCTGCTCTGGGAGATCCCTGATGTGTTGAAT
TCACTGGCGGTAGCTTGGATGATACTGAGAGCCATAACATTCACAACGACATCAAACGTGGTTGTTCCGCTGCTAGC
CCTGCTAACACCCGGGCTGAGATGCTTGAATCTGGATGTGTACAGGATACTGCTGTTGATGGTCGGAATAGGCAGCT
TGATCAGGGAGAAGAGGAGTGCAGCTGCAAAAAAGAAAGGAGCAAGTCTGCTATGCTTGGCTCTAGCCTCAACAGGA
CTTTTCAACCCCATGATCCTTGCTGCTGGACTGATTGCATGTGATCCCAACCGTAAACGCGGATGGCCCGCAACTGA
AGTGATGACAGCTGTCGGCCTAATGTTTGCCATCGTCGGAGGGCTGGCAGAGCTTGACATTGACTCCATGGCCATTC
CAATGACTATCGCGGGGCTCATGTTTGCTGCTTTCGTGATTTCTGGGAAATCAACAGATATGTGGATTGAGAGAACG
GCGGACATTTCCTGGGAAAGTGATGCAGAAATTACAGGCTCGAGCGAAAGAGTTGATGTGCGGCTTGATGATGATGG
AAACTTCCAGCTCATGAATGATCCAGGAGCACCTTGGAAGATATGGATGCTCAGAATGGTCTGTCTCGCGATTAGTG
CGTACACCCCCTGGGCAATCTTGCCCTCAGTAGTTGGATTTTGGATAACTCTCCAATACACAAAGAGAGGAGGCGTG
TTGTGGGACACTCCCTCACCAAAGGAGTACAAAAAGGGGGACACGACCACCGGCGTCTACAGGATCATGACTCGTGG
GCTGCTCGGCAGTTATCAAGCAGGAGCGGGCGTGATGGTTGAAGGTGTTTTCCACACCCTTTGGCATACAACAAAAG
GAGCCGCTTTGATGAGCGGAGAGGGCCGCCTGGACCCATACTGGGGCAGTGTCAAGGAGGATCGACTTTGTTACGGA
GGACCCTGGAAATTGCAGCACAAGTGGAACGGGCAGGATGAGGTGCAGATGATTGTGGTGGAACCTGGCAAGAACGT
TAAGAACGTCCAGACGAAACCAGGGGTGTTCAAAACACCTGAAGGAGAAATCGGGGCCGTGACTTTGGACTTCCCCA
CTGGAACATCAGGCTCACCAATAGTGGACAAAAACGGTGATGTGATTGGGCTTTATGGCAATGGAGTCATAATGCCC
AACGGCTCATACATAAGCGCGATAGTGCAGGGTGAAAGGATGGATGAGCCAATCCCAGCCGGATTCGAACCTGAGAT
GCTGAGGAAAAAACAGATCACTGTACTGGATCTCCATCCCGGCGCCGGTAAAACAAGGAGGATTCTGCCACAGATCA
TCAAAGAGGCCATAAACAGAAGACTGAGAACAGCCGTGCTAGCACCAACCAGGGTTGTGGCTGCTGAGATGGCTGAA
GCACTGAGAGGACTGCCCATCCGGTACCAGACATCCGCAGTGCCCAGAGAACATAATGGAAATGAGATTGTTGATGT
CATGTGTCATGCTACCCTCACCCACAGGCTGATGTCTCCTCACAGGGTGCCGAACTACAACCTGTTCGTGATGGATG
AGGCTCATTTCACCGACCCAGCTAGCATTGCAGCAAGAGGTTACATTTCCACAAAGGTCGAGCTAGGGGAGGCGGCG
GCAATATTCATGACAGCCACCCCACCAGGCACTTCAGATCCATTCCCAGAGTCCAATTCACCAATTTCCGACTTACA
GACTGAGATCCCGGATCGAGCTTGGAACTCTGGATACGAATGGATCACAGAATACACCGGGAAGACGGTTTGGTTTG
TGCCTAGTGTCAAGATGGGGAATGAGATTGCCCTTTGCCTACAACGTGCTGGAAAGAAAGTAGTCCAATTGAACAGA
AAGTCGTACGAGACGGAGTACCCAAAATGTAAGAACGATGATTGGGACTTTGTTATCACAACAGACATATCTGAAAT
GGGGGCTAACTTCAAGGCGAGCAGGGTGATTGACAGCCGGAAGAGTGTGAAACCAACCATCATAACAGAAGGAGAAG
GGAGAGTGATCCTGGGAGAACCATCTGCAGTGACAGCAGCTAGTGCCGCCCAGAGACGTGGACGTATCGGTAGAAAT
CCGTCGCAAGTTGGTGATGAGTACTGTTATGGGGGGCACACGAATGAAGACGACTCGAACTTCGCCCATTGGACTGA
GGCACGAATCATGCTGGACAACATCAACATGCCAAACGGACTGATCGCTCAATTCTACCAACCAGACGCGTGAGAAGG
TATATACCATGGATGGGGAATACCGGCTCAGAGGAGAAGAGAGAAAAAACTTTCTGGAACTGTTGAGGACTGCAGAT
CTGCCAGTTTGGCTGGCTTACAAGGTTGCAGCGGCTGGAGTGTCATACCACGACCGGAGGTGGTGCTTTGATGGTCC
TAGGACAAACACAATTTTAGAAGACAACAACGAAGTGGAAGTCATCACGAAGCTTGGTGAAAGGAAGATTCTGAGGC
CGCGCTGGATTGACGCCAGGGTGTACTCGGATCACCAGGCACTAAAGGCGTTCAAGGACTTCGCCTCGGGAAAACGT
TCTCAGATAGGGCTCATTGAGGTTCTGGGAAAGATGCCTGAGCACTTCATGGGGAAGACATGGGAAGCACTTGACAC
CATGTACGTTGTGGCCACTGCAGAGAAAGGAGGAAGAGCTCACAGAATGGCCCTGGAGGAACTGCCAGATGCTCTTC
AGACAATTGCCTTGATTGCCTTATTGAGTGTGATGACCATGGGAGTATTCTTCCTCCTCATGCAGCGGAAGGGCATT
GGAAAGATAGGTTTGGGAGGCGCTGTCTTGGGAGTCGCGACCTTTTTCTGTTGGATGGCTGAAGTTCCAGGAACGAA
GATCGCCGGAATGTTGCTGCTCTCCCTTCTCTTGATGATTGTGCTAATTCCTGAGCCAGACAGACGAACGTTCGCAGA
CAGACAACCAGCTAGCCGTGTTCCTGATTTGTGTCATGACCCTTGTGAGCGCAGTGGCAGCCAACGAGATGGGTTGG
CTAGATAAGACCAAGAGTGACATAAGCAGTTTGTTTGGGCAAAGAATTGAGGTCAAGGAGAATTTCAGCATGGGAGA
GTTTCTTCTGGACTTGAGGCCGGCAACAGCCTGGTCACTGTACGCTGTGACAACAGCGGTCCTCACTCCACTGCTAA
AGCATTTGATCACGTCAGATTACATCAACACCTCATTGACCTCAATAAACGTTCAGGCAAGTGCACTATTCACACTC
GCGCGAGGCTTCCCCTTCGTCGATGTTGGAGTGTCGGCTCTCCTGCTAGCAGCCGGATGCTGGGGACAAGTCACCCT
CACCGTTACGGTAACAGCGGCAACACTCCTTTTTTGCCACTATGCCTACATGGTTCCCGGTTGGCAAGCTGAGGCAA
TGCGCTCAGCCCAGCGGCGGACAGCGGCCGGAATCATGAAGAACGCTGTAGTGGATGGCATCGTGGCCACGGACGTC
CCAGAATTAGAGCGCACCACACCCATCATGCAGAAGAAAGTTGGACAGATCATGCTGATCTTGGTGTCTCTAGCTGC
AGTAGTAGTGAACCCGTCTGTGAAGCAGTACGAGAAGCCGGAATTTTGATCACGGCCGCAGCGGTGACGCTTGGG
AGAATGGAGCAAGCTCTGTTTGGAACGCAACAACTGCCATCGGACTCTGCCACATCATGCGTGGGGGTTGGTTGTCA
TGTCTATCCATAACATGGACACTCATAAAGAACATGGAAAAACCAGGACTAAAAAGAGGGTGGGGCAAAAGGACGCAC
CTTGGGAGAGGTTTGGAAAGAAAGACTCAACCAGATGACAAAAGAAGAGTTCACTAGGTACCGCAAAGAGGCCATCA
TCGAAGTCGATCGCTCAGCGGCAAAACACGCCAGGAAAGAAGGCAATGTCACTGGAGGGCATCCAGTCTCTAGGGGC
ACAGCAAAACTGAGATGGCTGGTCGAACGGAGGTTTCTCGAACCGGTCGGAAAAGTGATTGACCTTGGATGTGGAAG
```

FIG. 1C

```
AGGCGGTTGGTGTTACTATATGGCAACCCAAAAAAGAGTCCAAGAAGTCAGAGGGTACACAAAGGGCGGTCCCGGAC
ATGAAGAGCCCCAACTAGTGCAAAGTTATGGATGGAACATTGTCACCATGAAGAGTGGAGTGGATGTGTTCTACAGA
CCTTCTGAGTGTTGTGACACCCTCCTTTGTGACATCGGAGAGTCCTCGTCAAGTGCTGAGGTTGAAGAGCATAGGAC
GATTCGGGTCCTTGAAATGGTTGAGGACTGGCTGCACCGAGGGCCAAGGGAATTTTGCGTGAAGGTGCTCTGCCCCT
ACATGCCGAAAGTCATAGAGAAGATGGAGCTGCTCCAACGCCGGTATGGGGGGGGACTGGTCAGAAACCCACTCTCA
CGGAATTCCACGCACGAGATGTATTGGGTGAGTCGAGCTTCAGGCAATGTGGTACATTCAGTGAATATGACCAGCCA
GGTGCTCCTAGGAAGAATGGAAAAAAGGACCTGGAAGGGACCCCAATACGAGGAAGATGTAAACTTGGGAAGTGGAA
CCAGGGCGGTGGGAAAACCCCTGCTCAACTCAGACACCAGTAAAATCAAGAACAGGATTGAACGACTCAGGCGTGAG
TACAGTTCGACGTGGCACCACGATGAGAACCACCCATATAGAACCTGGAACTATCACGGCAGTTATGATGTGAAGCC
CACAGGCTCCGCCAGTTCGCTGGTCAATGGAGTGGTCAGGCTCCTCTCAAAACCATGGGACACCATCACGAATGTTA
CCACCATGGCCATGACTGACACTACTCCCTTCGGGCAGCAGCGAGTGTTCAAAGAGAAGGTGGACACGAAAGCTCCT
GAACCGCCAGAAGGAGTGAAGTACGTGCTCAACGAGACCACCAACTGGTTGTGGGCGTTTTTGGCCAGAGAAAAACG
TCCCAGAATGTGCTCTCGAGAGGAATTCATAAGAAAGGTCAACAGCAATGCAGCTTTGGGTGCCATGTTTGAAGAGC
AGAATCAATGGAGGAGCGCCAGAGAAGCAGTTGAAGATCCAAAATTTTGGGAGATGGTGGATGAGGAGCGCGAGGCA
CATCTGCGGGGGGAATGTCACACTTGCATTTACAACATGATGGGAAAGAGAGAGAAAAAACCCGGAGAGTTCGGAAA
GGCCAAGGGAAGCAGAGCCATTTGGTTCATGTGGCTCGGAGCTCGCTTTCTGGAGTTCGAGGCTCTGGGTTTTCTCA
ATGAAGACCACTGGCTTGGAAGAAAGAACTCAGGAGGAGGTGTCGAGGGCTTGGGCCTCCAAAAACTGGGTTACATC
CTGCGTGAAGTTGGCACCCGGCCTGGGGGCAAGATCTATGCTGATGACACAGCTGGCTGGGACACCCGCATCACGAG
AGCTGACTTGGAAAATGAAGCTAAGGTGCTTGAGCTGCTTGATGGGGAACATCGGCGTCTTGCCAGGGCCATCATTG
AGCTCACCTATCGTCACAAAGTTGTGAAAGTGATGCGCCCGGCTGCTGATGGAAGAACCGTCATGGATGTTATCTCC
AGAGAAGATCAGAGGGGGAGTGGACAAGTTGTCACCTACGCCCTAAACACTTTCACCAACCTGGCCGTCCAGCTGGT
GAGGATGATGGAAGGGGAAGGAGTGATTGGCCCAGATGATGTGGAGAAACTCACAAAAGGGAAAGGACCCAAAGTCA
GGACCTGGCTGTTTGAGAATGGGGAAGAAAGACTCAGCCGCATGGCTGTCAGTGGAGATGACTGTGTGGTAAAGCCC
CTGGACGATCGCTTTGCCACCTCGCTCCACTTCCTCAATGCTATGTCAAAGGTTCGCAAAGACATCCAAGAGTGGAA
ACCGTCAACTGGATGGTATGATTGGCAGCAGGTTCCATTTTGCTCAAACCATTTCACTGAATTGATCATGAAAGATG
GAACAACACTGGTGGTTCCATGCCGAGGACAGGATGAATTGGTAGGCAGAGCTCGCATATCTCCAGGGGCCGGATGG
AACGTCCGCGACACTGCTTGTCTGGCTAAGTCTTATGCCCAGATGTGGCTGCTTCTGTACTTCCACAGAAGAGACCT
GCGGCTCATGGCCAACGCCATTTGCTCCGCTGTCCCTGTGAATTGGGTCCCTACCGGAAGAACCACGTGGTCCATCC
ATGCAGGAGGAGAGTGGATGACAACAGAGGACATGTTGGAGGTCTGGAACCGTGTTTGGATAGAGGAGAATGAATGG
ATGGAAGACAAAACCCCAGTGGAGAAATGGAGTGACGTCCCATATTCAGGAAAACGAGAGGACATCTGGTGTGGCAG
CCTGATTGGCACAAGAGCCCGAGCCACGTGGGCAGAAAACATCCAGGTGGCTATCAACCAAGTCAGAGCAATCATCG
GAGATGAGAAGTATGTGGATTACATGAGTTCACTAAAGAGATATGAAGACACAACTTTGGTTGAGGACACAGTACTG
TAGATATTTAATCAATTGTAAATAGACAATATAAGTATGCATAAAAGTGTAGTTTTATAGTAGTATTTAGTGGTGTT
AGTGTAAATAGTTAAGAAAATTTTGAGGAGAAAGTCAGGCCGGGAAGTTCCCGCCACCGGAAGTTGAGTAGACGGTG
CTGCCTGCGACTCAACCCCAGGAGGACTGGGTGAACAAAGCCGCGAAGTGATCCATGTAAGCCCTCAGAACCGTCTC
GGAAGGAGGACCCCACATGTTGTAACTTCAAAGCCCAATGTCAGACCACGCTACGGCGTGCTACTCTGCGGAGAGTG
CAGTCTGCGATAGTGCCCCAGGAGGACTGGGTTAACAAAGGCAAACCAACGCCCCACGCGGCCCTAGCCCCGGTAAT
GGTGTTAACCAGGGCGAAAGGACTAGAGGTTAGAGGAGACCCCGCGGTTTAAAGTGCACGGCCCAGCCTGGCTGAAG
CTGTAGGTCAGGGGAAGGACTAGAGGTTAGTGGAGACCCCGTGCCACAAAACACCACAACAAAACAGCATATTGACA
CCTGGGATAGACTAGGAGATCTTCTGCTCTGCACAACCAGCCACACGGCACAGTGCGCCGACAATGGTGGCTGGTGG
TGCGAGAACACAGGATCT-3'
```

OLIGONUCLEOTIDES AND METHODS FOR DETECTION OF WEST NILE VIRUS

FIELD OF THE INVENTION

The present invention relates to methods and reagents for detecting West Nile virus. More particularly, the invention relates to nucleic acid-based methods of detecting West Nile virus and nucleic acid reagents useful in such methods.

BACKGROUND OF THE INVENTION

West Nile Virus is a spherical, enveloped virus containing a single-stranded positive polarity RNA genome of approximately 11 kilobases. West Nile Virus subtypes are distinguishable by antigenic variations in the envelope (E or ENV) protein and by the presence of an N-glycosylation site (Asn-Tyr-Ser) at amino acids 154-156 (Jia, 1999, Lancet. 354; 1971-2). West Nile virus is taxonomically classified within the family Flaviviridae, genus *Flavivirus*. The virus was originally isolated in 1937 from a febrile human who resided in the West Nile District of Uganda.

West Nile virus can be transmitted to humans and domestic animals through mosquitoes and migratory birds that serve as amplifying hosts. Although West Nile virus infection is generally asymptomatic in areas of the world where the virus is endemic, infected humans can incur a mild fever, rash, nausea, headache, disorientation and back pain. More serious complications from West Nile virus infection include hepatitis, pancreatitis, encephalitis, myocarditis, meningitis, neurologic infection, and death.

West Nile virus is geographically distributed in Africa, the Middle East, western and central Asia, India, Australia (Kunjin virus) and Europe. The first recorded epidemic occurred in Israel in the early 1950's. More recently, outbreaks of human encephalitis caused by West Nile virus have been documented in Romania and Russia. West Nile virus, introduced recently into the northeastern United States, caused seven human deaths in New York City and surrounding areas in 1999. A relatively large number of birds, particularly crows, and horses also died. The subsequent recovery of West Nile virus from mosquitoes and birds in 2000 confirmed that the virus had become established in the northeastern United States. (Anderson et al. Proc. Nat'l Acad. Sci. USA 98(23): 12885-12889, 2001).

In an attempt to prevent the spread of West Nile virus through control of larval and adult mosquitoes, mapping, spraying and removal of breeding sites has been initiated in states where West Nile virus has been identified. Despite these efforts, West Nile virus remains a threat due to its mode of transmission. At present, there is no vaccine or other known treatment for West Nile virus infection. Accordingly there remains an unmet need for reagents and methods for the diagnosis of West Nile virus infection.

During the 2002 epidemic of West Nile virus in the United States, twenty-three persons were reported to have acquired West Nile virus infection after receipt of blood components from donors infected with the virus (Morbidity and Mortality Weekly Report, 52(32): 769-772, 2003). Consequently, there is also a need for reagents and tests for diagnosing West Nile virus infection that can be used with blood or blood components such as plasma to identify infected blood.

Detection of West Nile virus using PCR-based assays has been reported. Russian patent application RU2199589, published Feb. 27, 2003, discloses a PCR-based method for detection of West Nile virus in which a double amplification assay produces a 495 base pair PCR product that is analyzed by agarose gel (from English language abstract).

WO 02/081511, published Oct. 17, 2002, assigned to Institute Pasteur and Kimron Veterinary Institute, discloses a neuroinvasive and neurovirulent strain of the West Nile virus, known as IS-98-ST1, nucleic acid molecules derived from the genome thereof and methods of detecting West Nile virus.

Anderson et al., Science 286: 2331-2333, 1999 discloses primers for amplifying a 921 base portion of the genome of West Nile virus. Lanciotti et al., J. Clin. Microbiol. 38(11): 4066-4071 discloses a PCR assay for detecting West Nile virus wherein the primers were selected from the envelope (ENV) and 3' non-coding regions. Briese, T. et al., Emerging Infectious Diseases 8(5) May 2002 discloses a PCR assay for detecting West Nile virus wherein the primers were selected from the E gene. Huang et al. Emerging Infectious Diseases, 8(12) December 2002, discloses a PCR assay for detection of West Nile virus wherein the primers were selected from the $NS_5$ (non-structural protein 5) and ENV genes.

SUMMARY OF THE INVENTION

The invention provides methods and oligonucleotide reagents for detecting West Nile virus.

The invention provides isolated oligonucleotides comprising
(a) $R_1$—N—$R_2$ wherein
  N is an oligonucleotide selected from the group consisting of

| | |
|---|---|
| 5'-CTGGATCGATGGAGAGGTGT-3', | (SEQ ID NO: 2) |
| 5'-TCCGGTCTTTCCTCCTCTTT-3', | (SEQ ID NO: 3) |
| 5'-CTACCGTCAGCGATCTCTCC-3', | (SEQ ID NO: 4) |
| 5'-TTCCTTTGCCAAATAGTCCG-3', | (SEQ ID NO: 5) |
| 5'-GACGTCGGGTCATTTGAAGT-3' | (SEQ ID NO: 6) |
| 5'-ACTGCAATTCCAACACCACA-3', | (SEQ ID NO: 7) |
| 5'-ATGTCCTGGATAACGCAAGG-3', | (SEQ ID NO: 8) |
| 5'-CTCCTCCAACTGCGAGAAAC-3', | (SEQ ID NO: 9) |
| 5'-ATCGCGCTTGGAATAGCTTA-3', | (SEQ ID NO: 10) |
| 5'-GACAGCCGTTCCAATGATCT-3', | (SEQ ID NO: 11) |
| 5'-AGGCCGGGTAGAGATTGACT-3', | (SEQ ID NO: 12) |
| 5'-CCTGCAGCACCAATCTGTTA-3', | (SEQ ID NO: 13) |
| 5'-CAGTGTTTATGGTGGCATCG-3', | (SEQ ID NO: 14) |
| 5'-GGCATCGTGATAAGCCATTT-3', | (SEQ ID NO: 15) |
| 5'-TGGCAGAGCTTGACATTGAC-3', | (SEQ ID NO: 16) |
| 5'-GCCGTTCTCTCAATCCACAT-3', | (SEQ ID NO: 17) |
| 5'-ATACTGGGGCAGTGTCAAGG-3', | (SEQ ID NO: 18) |
| 5'-TAACGTTCTTGCCAGGTTCC-3', | (SEQ ID NO: 19) |
| 5'-GGCTGAAGCACTGAGAGGAC-3', | (SEQ ID NO: 20) |
| 5'-ACAGGTTGTAGTTCGGCACC-3', | (SEQ ID NO: 21) |
| 5'-CCAGGCACTTCAGATCCATT-3', | (SEQ ID NO: 22) |

-continued

| Sequence | |
|---|---|
| 5'-CTAGGCACAAACCAAACCGT-3', | (SEQ ID NO: 23) |
| 5'-GATTGACGCCAGGGTGTACT-3', | (SEQ ID NO: 24) |
| 5'-ATGTCTTCCCCATGAAGTGC-3', | (SEQ ID NO: 25) |
| 5'-CGCAGACAGACAACCAGCTA-3', | (SEQ ID NO: 26) |
| 5'-TTGACCTCAATTCTTTGCCC-3', | (SEQ ID NO: 27) |
| 5'-GACGTCCCAGAATTAGAGCGC-3', | (SEQ ID NO: 28) |
| 5'-TCCGGCTTCTCGTACTGTCT-3', | (SEQ ID NO: 29) |
| 5'-CTCTGTTTGGAACGCAACAA-3', | (SEQ ID NO: 30) |
| 5'-GCCCCACCTCTTTTTAGTCC-3', | (SEQ ID NO: 31) |
| 5'-AGTCGAGCTTCAGGCAATGT-3', | (SEQ ID NO: 32) |
| 5'-TGGTGTCTGAGTTGAGCAGG-3', | (SEQ ID NO: 33) |
| 5'-TGAGTACAGTTCGACGTGGC-3', | (SEQ ID NO: 34) |
| 5'-TTGAGAGGAGCCTGACCACT-3', | (SEQ ID NO: 35) |
| 5'-AGCTAAGGTGCTTGAGCTGC-3', | (SEQ ID NO: 36) |
| 5'-ATGACGGTTCTTCCATCAGC-3', | (SEQ ID NO: 37) |
| 5'-ACATCCAAGAGTGGAAACCG-3', | (SEQ ID NO: 38) |
| 5'-CGAGCTCTGCCTACCAATTC-3', | (SEQ ID NO: 39) |
| 5'-GCAGGAGGAGAGTGGATGAC-3', | (SEQ ID NO: 40) |
| 5'-TTCTCCACTGGGGTTTTGTC-3', | (SEQ ID NO: 41) |
| 5'-GGGTTAACAAAGGCAAACCA-3', | (SEQ ID NO: 42) |
| 5'-CCCTGACCTACAGCTTCAG-3', | (SEQ ID NO: 43) |
| 5'-TAGTTCGCCTGTGTGAGCTG-3', | (SEQ ID NO: 44) |
| 5'-TTTTAGCATATTGACAGCCCG-3', | (SEQ ID NO: 45) |
| 5'-TTGATTGGACTGAAGAGGGC-3', | (SEQ ID NO: 46) |
| 5'-GCAATTGCTGTGAACCTGAA-3', | (SEQ ID NO: 47) |
| 5'-GCTGAAGCTGTAGGTCAGGG-3', | (SEQ ID NO: 48) |
| 5'-CTGGTTGTGCAGAGCAGAAG-3', | (SEQ ID NO: 49) |
| 5'-GGAGAGTGCAGTCTGCGATA-3', | (SEQ ID NO: 50) |
| 5'-GTCTCCTCTAACCTCTAGTCC-3', | (SEQ ID NO: 51) |
| 5'-GCCACCGGAAGTTGAGTAGA-3', | (SEQ ID NO: 52) |
| 5'-GAGACGGTTCTGAGGGCTTAC-3', | (SEQ ID NO: 53) |
| 5'-TGGATTTGGTCTCACCAGCACTCGGAT GTT-3', | (SEQ ID NO: 54) |
| 5'-ACATCCGCAGTGCCCAGAGAACATAAT GGA-3', | (SEQ ID NO: 55) |
| 5'-ACGGGTTCACTACTACTGCATCTAGAG ACA-3', | (SEQ ID NO: 56) |
| 5'-CCGGTAATGGTGTTAAACCAGGGCGAA AGGA-3', | (SEQ ID NO: 57) |
| 5'-CAGGAGGACTGGGTTAACAAAGGCAAA CCA-3', and | (SEQ ID NO: 58) |
| 5'-ATCACTTCGCGGCTTTGTTCACCCAGT CCT-3'; | (SEQ ID NO: 59) |

$R_1$ is an oligonucleotide sequence of 0-20 contiguous bases of the West Nile virus consensus sequence shown in FIG. 1 (SEQ ID NO: 1) immediately upstream of the 5' end of N in said consensus sequence covalently linked to N at the 5' end, provided that when N is complementary to said consensus sequence, $R_1$ is selected from the complement of said consensus sequence; and $R_2$ is an oligonucleotide sequence of 0-20 contiguous bases of said consensus sequence immediately downstream of the 3'-end of N in said consensus sequence covalently linked to N at the 3' end, provided that when N is complementary to said consensus sequence, $R_2$ is selected from the complement of said consensus sequence;

(b) an isolated fragment of N as defined in (a) wherein said fragment is 10-19 bases in length;

(c) $R_1$—X—$R_2$, wherein X is at least 10 contiguous bases of N as defined in (a), and $R_1$ and $R_2$ are as defined in (a), wherein when $R_1$ is present, $R_2$ is absent and X is selected such that the base at the 5'-end of X is the same as the base at the 5'-end of N; and when $R_2$ is present, $R_1$ is absent and X is selected such that the base at the 3'-end of X is the same as the base at the 3'-end of N;

(d) an isolated oligonucleotide which has at least 80% sequence identity with an oligonucleotide of (a), (b) or (c); or (e) an isolated oligonucleotide which is the full-length complement of (a), (b), (c) or (d).

Preferably, the oligonucleotides of the invention comprise, or consist of, an oligonucleotide selected from the group consisting of

| Sequence | |
|---|---|
| 5'-CTGGATCGATGGAGAGGTGT-3', | (SEQ ID NO: 2) |
| 5'-TCCGGTCTTTCCTCCTCTTT-3', | (SEQ ID NO: 3) |
| 5'-CTACCGTCAGCGATCTCTCC-3', | (SEQ ID NO: 4) |
| 5'-TTCCTTTGCCAAATAGTCCG-3', | (SEQ ID NO: 5) |
| 5'-GACGTCGGGTCATTTGAAGT-3', | (SEQ ID NO: 6) |
| 5'-ACTGCAATTCCAACACCACA-3', | (SEQ ID NO: 7) |
| 5'-ATGTCCTGGATAACGCAAGG-3', | (SEQ ID NO: 8) |
| 5'-CTCCTCCAACTGCGAGAAAC-3', | (SEQ ID NO: 9) |
| 5'-ATCGCGCTTGGAATAGCTTA-3', | (SEQ ID NO: 10) |
| 5'-GACAGCCGTTCCAATGATCT-3', | (SEQ ID NO: 11) |
| 5'-AGGCCGGGTAGAGATTGACT-3', | (SEQ ID NO: 12) |
| 5'-CCTGCAGCACCAATCTGTTA-3', | (SEQ ID NO: 13) |
| 5'-CAGTGTTTATGGTGGCATCG-3', | (SEQ ID NO: 14) |
| 5'-GGCATCGTGATAAGCCATTT-3', | (SEQ ID NO: 15) |
| 5'-TGGCAGAGCTTGACATTGAC-3', | (SEQ ID NO: 16) |
| 5'-GCCGTTCTCTCAATCCACAT-3', | (SEQ ID NO: 17) |
| 5'-ATACTGGGGCAGTGTCAAGG-3', | (SEQ ID NO: 18) |
| 5'-TAACGTTCTTGCCAGGTTCC-3', | (SEQ ID NO: 19) |
| 5'-GGCTGAAGCACTGAGAGGAC-3', | (SEQ ID NO: 20) |
| 5'-ACAGGTTGTAGTTCGGCACC-3', | (SEQ ID NO: 21) |

-continued

| | |
|---|---|
| 5'-CCAGGCACTTCAGATCCATT-3', | (SEQ ID NO: 22) |
| 5'-CTAGGCACAAACCAAACCGT-3', | (SEQ ID NO: 23) |
| 5'-GATTGACGCCAGGGTGTACT-3', | (SEQ ID NO: 24) |
| 5'-ATGTCTTCCCCATGAAGTGC-3', | (SEQ ID NO: 25) |
| 5'-CGCAGACAGACAACCAGCTA-3', | (SEQ ID NO: 26) |
| 5'-TTGACCTCAATTCTTTGCCC-3', | (SEQ ID NO: 27) |
| 5'-GACGTCCCAGAATTAGAGCGC-3', | (SEQ ID NO: 28) |
| 5'-TCCGGCTTCTCGTACTGTCT-3', | (SEQ ID NO: 29) |
| 5'-CTCTGTTTGGAACGCAACAA-3', | (SEQ ID NO: 30) |
| 5'-GCCCCACCTCTTTTTAGTCC-3', | (SEQ ID NO: 31) |
| 5'-AGTCGAGCTTCAGGCAATGT-3', | (SEQ ID NO: 32) |
| 5'-TGGTGTCTGAGTTGAGCAGG-3', | (SEQ ID NO: 33) |
| 5'-TGAGTACAGTTCGACGTGGC-3', | (SEQ ID NO: 34) |
| 5'-TTGAGAGGAGCCTGACCACT-3', | (SEQ ID NO: 35) |
| 5'-AGCTAAGGTGCTTGAGCTGC-3', | (SEQ ID NO: 36) |
| 5'-ATGACGGTTCTTCCATCAGC-3', | (SEQ ID NO: 37) |
| 5'-ACATCCAAGAGTGGAAACCG-3', | (SEQ ID NO: 38) |
| 5'-CGAGCTCTGCCTACCAATTC-3', | (SEQ ID NO: 39) |
| 5'-GCAGGAGGAGAGTGGATGAC-3', | (SEQ ID NO: 40) |
| 5'-TTCTCCACTGGGGTTTTGTC-3', | (SEQ ID NO: 41) |
| 5'-GGGTTAACAAAGGCAAACCA-3', | (SEQ ID NO: 42) |
| 5'-CCCTGACCTACAGCTTCAG-3', | (SEQ ID NO: 43) |
| 5'-TAGTTCGCCTGTGTGAGCTG-3', | (SEQ ID NO: 44) |
| 5'-TTTTAGCATATTGACAGCCCG-3', | (SEQ ID NO: 45) |
| 5'-TTGATTGGACTGAAGAGGGC-3', | (SEQ ID NO: 46) |
| 5'-GCAATTGCTGTGAACCTGAA-3', | (SEQ ID NO: 47) |
| 5'-GCTGAAGCTGTAGGTCAGGG-3', | (SEQ ID NO: 48) |
| 5'-CTGGTTGTGCAGAGCAGAAG-3', | (SEQ ID NO: 49) |
| 5'-GGAGAGTGCAGTCTGCGATA-3', | (SEQ ID NO: 50) |
| 5'-GTCTCCTCTAACCTCTAGTCC-3', | (SEQ ID NO: 51) |
| 5'-GCCACCGGAAGTTGAGTAGA-3', and | (SEQ ID NO: 52) |
| 5'-GAGACGGTTCTGAGGGCTTAC-3'. | (SEQ ID NO: 53) |

More preferably the oligonucleotides of the invention comprise an oligonucleotide selected from the group consisting of

| | |
|---|---|
| 5'-ATCGCGCTTGGAATAGCTTA-3', | (SEQ ID NO: 10) |
| 5'-GACAGCCGTTCCAATGATCT-3', | (SEQ ID NO: 11) |
| 5'-GGCTGAAGCACTGAGAGGAC-3', | (SEQ ID NO: 20) |
| 5'-ACAGGTTGTAGTTCGGCACC-3', | (SEQ ID NO: 21) |
| 5'-GACGTCCCAGAATTAGAGCGC-3', | (SEQ ID NO: 28) |
| 5'-TCCGGCTTCTCGTACTGTCT-3', | (SEQ ID NO: 29) |
| 5'-GGGTTAACAAAGGCAAACCA-3', | (SEQ ID NO: 42) |
| 5'-CCCTGACCTACAGCTTCAG-3', | (SEQ ID NO: 43) |
| 5'-GGAGAGTGCAGTCTGCGATA-3', | (SEQ ID NO: 50) |
| 5'-GTCTCCTCTAACCTCTAGTCC-3', | (SEQ ID NO: 51) |
| 5'-GCCACCGGAAGTTGAGTAGA-3', and | (SEQ ID NO: 52) |
| 5'-GAGACGGTTCTGAGGGCTTAC-3'. | (SEQ ID NO: 53) |

Most preferably the invention provides oligonucleotides comprising an oligonucleotide selected from the group consisting of

| | |
|---|---|
| 5'-GACGTCCCAGAATTAGAGCGC-3', | (SEQ ID NO: 28) |
| 5'-TCCGGCTTCTCGTACTGTCT-3', | (SEQ ID NO: 29) |
| 5'-GCCACCGGAAGTTGAGTAGA-3', and | (SEQ ID NO: 52) |
| 5'-GAGACGGTTCTGAGGGCTTAC-3'. | (SEQ ID NO: 53) |

In other preferred embodiments, the invention provides oligonucleotides comprising, or consisting of, an oligonucleotide selected from the group consisting of

| | |
|---|---|
| 5'-TGGATTTGGTCTCACCAGCACTCGGATGTT-3', | (SEQ ID NO: 54) |
| 5'-ACATCCGCAGTGCCCAGAGAACATAATGGA-3', | (SEQ ID NO: 55) |
| 5'-ACGGGTTCACTACTACTGCATCTAGAGACA-3', | (SEQ ID NO: 56) |
| 5'-CCGGTAATGGTGTTAAACCAGGGCGAAAGGA-3', | (SEQ ID NO: 57) |
| 5'-CAGGAGGACTGGGTTAACAAAGGCAAACCA-3', and | (SEQ ID NO: 58) |
| 5'-ATCACTTCGCGGCTTTGTTCACCCAGTCCT-3'. | (SEQ ID NO: 59) |

More preferably, the oligonucleotide comprises

| | |
|---|---|
| 5'-ACGGGTTCACTACTACTGCATCTAGAGACA-3', or | (SEQ ID NO: 56) |
| 5'-ATCACTTCGCGGCTTTGTTCACCCAGTCCT-3'. | (SEQ ID NO: 59) |

The oligonucleotides of the invention can further comprise a detectable label. Preferably, the detectable label comprises a fluorescent molecule attached at the 5' end. More preferably, the oligonucleotides of the invention further comprise a quencher molecule attached at the 3' end.

Another aspect of the invention provides pairs of isolated oligonucleotide sequences selected from the group consisting of

| | |
|---|---|
| (a) 5'-CTGGATCGATGGAGAGGTGT-3' and | (SEQ ID NO: 2) |
| 5'-TCCGGTCTTTCCTCCTCTTT-3' | (SEQ ID NO: 3) |

-continued (b) 5'-CTACCGTCAGCGATCTCTCC-3' and (SEQ ID NO: 4)
    5'-TTCCTTTGCCAAATAGTCCG-3'     (SEQ ID NO: 5)

(c) 5'-GACGTCGGGTCATTTGAAGT-3' and (SEQ ID NO: 6)
    5'-ACTGCAATTCCAACACCACA-3'     (SEQ ID NO: 7)

(d) 5'-ATGTCCTGGATAACGCAAGG-3' and (SEQ ID NO: 8)
    5'-CTCCTCCAACTGCGAGAAAC-3'     (SEQ ID NO: 9)

(e) 5'-ATCGCGCTTGGAATAGCTTA-3' and (SEQ ID NO: 10)
    5'-GACAGCCGTTCCAATGATCT-3'     (SEQ ID NO: 11)

(f) 5'-AGGCCGGGTAGAGATTGACT-3' and (SEQ ID NO: 12)
    5'-CCTGCAGCACCAATCTGTTA-3'     (SEQ ID NO: 13)

(g) 5'-CAGTGTTTATGGTGGCATCG-3' and (SEQ ID NO: 14)
    5'-GGCATCGTGATAAGCCATTT-3'     (SEQ ID NO: 15)

(h) 5'-TGGCAGAGCTTGACATTGAC-3' and (SEQ ID NO: 16)
    5'-GCCGTTCTCTCAATCCACAT-3'     (SEQ ID NO: 17)

(i) 5'-ATACTGGGGCAGTGTCAAGG-3' and (SEQ ID NO: 18)
    5'-TAACGTTCTTGCCAGGTTCC-3'     (SEQ ID NO: 19)

(j) 5'-GGCTGAAGCACTGAGAGGAC-3' and (SEQ ID NO: 20)
    5'-ACAGGTTGTAGTTCGGCACC-3'     (SEQ ID NO: 21)

(k) 5'-CCAGGCACTTCAGATCCATT-3' and (SEQ ID NO: 22)
    5'-CTAGGCACAAACCAAACCGT-3'     (SEQ ID NO: 23)

(l) 5'-GATTGACGCCAGGGTGTACT-3' and (SEQ ID NO: 24)
    5'-ATGTCTTCCCCATGAAGTGC-3'     (SEQ ID NO: 25)

(m) 5'-CGCAGACAGACAACCAGCTA-3' and (SEQ ID NO: 26)
    5'-TTGACCTCAATTCTTTGCCC-3'     (SEQ ID NO: 27)

(n) 5'-GACGTCCCAGAATTAGAGCGC-3' and (SEQ ID NO: 28)
    5'-TCCGGCTTCTCGTACTGTCT-3'     (SEQ ID NO: 29)

(o) 5'-CTCTGTTTGGAACGCAACAA-3' and (SEQ ID NO: 30)
    5'-GCCCCACCTCTTTTTAGTCC-3'     (SEQ ID NO: 31)

(p) 5'-AGTCGAGCTTCAGGCAATGT-3' and (SEQ ID NO: 32)
    5'-TGGTGTCTGAGTTGAGCAGG-3'     (SEQ ID NO: 33)

(q) 5'-TGAGTACAGTTCGACGTGGC-3' and (SEQ ID NO: 34)
    5'-TTGAGAGGAGCCTGACCACT-3'     (SEQ ID NO: 35)

(r) 5'-AGCTAAGGTGCTTGAGCTGC-3' and (SEQ ID NO: 36)
    5'-ATGACGGTTCTTCCATCAGC-3'     (SEQ ID NO: 37)

(s) 5'-ACATCCAAGAGTGGAAACCG-3' and (SEQ ID NO: 38)
    5'-CGAGCTCTGCCTACCAATTC-3'     (SEQ ID NO: 39)

(t) 5'-GCAGGAGGAGAGTGGATGAC-3' and (SEQ ID NO: 40)
    5'-TTCTCCACTGGGGTTTTGTC-3'     (SEQ ID NO: 41)

(u) 5'-GGGTTAACAAAGGCAAACCA-3' and (SEQ ID NO: 42)
    5'-CCCTGACCTACAGCTTCAG-3'      (SEQ ID NO: 43)

-continued (v) 5'-TAGTTCGCCTGTGTGAGCTG-3' and (SEQ ID NO: 44)
    5'-TTTTAGCATATTGACAGCCCG-3'    (SEQ ID NO: 45)

(w) 5'-TTGATTGGACTGAAGAGGGC-3' and (SEQ ID NO: 46)
    5'-GCAATTGCTGTGAACCTGAA-3'     (SEQ ID NO: 47)

(x) 5'-GCTGAAGCTGTAGGTCAGGG-3' and (SEQ ID NO: 48)
    5'-CTGGTTGTGCAGAGCAGAAG-3'     (SEQ ID NO: 49)

(y) 5'-GGAGAGTGCAGTCTGCGATA-3' and (SEQ ID NO: 50)
    5'-GTCTCCTCTAACCTCTAGTCC-3'    (SEQ ID NO: 51)

(z) 5'-GCCACCGGAAGTTGAGTAGA-3' and (SEQ ID NO: 52)
    5'-GAGACGGTTCTGAGGGCTTAC-3'.   (SEQ ID NO: 53)

More preferably the pair of isolated oligonucleotide sequences is selected from the group consisting of (e) 5'-ATCGCGCTTGGAATAGCTTA-3' and (SEQ ID NO: 10)
    5'-GACAGCCGTTCCAATGATCT-3'     (SEQ ID NO: 11)

(j) 5'-GGCTGAAGCACTGAGAGGAC-3' and (SEQ ID NO: 20)
    5'-ACAGGTTGTAGTTCGGCACC-3'     (SEQ ID NO: 21)

(n) 5'-GACGTCCCAGAATTAGAGCGC-3' and (SEQ ID NO: 28)
    5'-TCCGGCTTCTCGTACTGTCT-3'     (SEQ ID NO: 29)

(u) 5'-GGGTTAACAAAGGCAAACCA-3' and (SEQ ID NO: 42)
    5'-CCCTGACCTACAGCTTCAG-3'      (SEQ ID NO: 43)

(y) 5'-GGAGAGTGCAGTCTGCGATA-3' and (SEQ ID NO: 50)
    5'-GTCTCCTCTAACCTCTAGTCC-3'    (SEQ ID NO: 51)

(z) 5'-GCCACCGGAAGTTGAGTAGA-3' and (SEQ ID NO: 52)
    5'-GAGACGGTTCTGAGGGCTTAC-3'    (SEQ ID NO: 53)

Most preferably, the pair of isolated oligonucleotide is

5'-GACGTCCCAGAATTAGAGCGC-3' and    (SEQ ID NO: 28)
5'-TCCGGCTTCTCGTACTGTCT-3', or     (SEQ ID NO: 29)
5'-GCCACCGGAAGTTGAGTAGA-3' and     (SEQ ID NO: 52)
5'-GAGACGGTTCTGAGGGCTTAC-3'.       (SEQ ID NO: 53)

A further aspect of the invention provides sets of oligonucleotides selected from the group consisting of (aa) 5'-ATCGCGCTTGGAATAGCTTA-3',         (SEQ ID NO: 10)
     5'-TGGATTTGGTCTCACCAGCACTCGGA       (SEQ ID NO: 54)
     TGTT-3' optionally labeled
     with a detectable label, and

5'-GACAGCCGTTCCAATGATCT-3';         (SEQ ID NO: 11)

(bb) 5'-GGCTGAAGCACTGAGAGGAC-3',         (SEQ ID NO: 20)
     5'-ACATCCGCAGTGCCCAGAGAACATAA       (SEQ ID NO: 55)
     TGGA-3' optionally labeled
     with a detectable label, and

5'-ACAGGTTGTAGTTCGGCACC-3';         (SEQ ID NO: 21)

-continued (cc) 5'-GACGTCCCAGAATTAGAGCGC-3', (SEQ ID NO: 28)

5'-ACGGGTTCACTACTACTGCATCTAGA (SEQ ID NO: 56)
GACA-3' optionally labeled
with a detectable label, and

5'-TCCGGCTTCTCGTACTGTCT-3' (SEQ ID NO: 29)

(dd) 5'-GGGTTAACAAAGGCAAACCA-3', (SEQ ID NO: 42)

5'-CCGGTAATGGTGTTAAACCAGGGCGA (SEQ ID NO: 57)
AAGGA-3' optionally labeled
with a detectable label, and

5'-CCCTGACCTACAGCTTCAG-3' (SEQ ID NO: 43)

(ee) 5'-GGAGAGTGCAGTCTGCGATA-3', (SEQ ID NO: 50)

5'-CAGGAGGACTGGGTTAACAAAGGCAA (SEQ ID NO: 58)
ACCA-3' optionally labeled
with a detectable label, and

5'-GTCTCCTCTAACCTCTAGTCC-3'; (SEQ ID NO: 51)

(ff) 5'-GCCACCGGAAGTTGAGTAGA-3', (SEQ ID NO: 52)

5'-ATCACTTCGCGGCTTTGTTCACCCAG (SEQ ID NO: 59)
TCCT-3' optionally labeled
with a detectable label, and

5'-GAGACGGTTCTGAGGGCTTAC-3'. (SEQ ID NO: 53)

More preferably the set is (cc) 5'-GACGTCCCAGAATTAGAGCGC-3' (SEQ ID NO: 28)

5'-ACGGGTTCACTACTACTGCATCTAGA (SEQ ID NO: 56)
GACA-3' optionally labeled
with a detectable label, and 5'-TCCGGCTTCTCGTACTGTCT-3' or (SEQ ID NO: 29)

(ff) 5'-GCCACCGGAAGTTGAGTAGA-3', (SEQ ID NO: 52)

5'-ATCACTTCGCGGCTTTGTTCACCCAG
TCCT-3' optionally labeled (SEQ ID NO: 59)
with a detectable label, and

5'-GAGACGGTTCTGAGGGCTTAC-3'. (SEQ ID NO: 53)

The invention additionally provides methods of detecting West Nile virus in a test sample comprising the steps of amplifying West Nile Virus nucleic acid in said test sample; and detecting amplified nucleic acid, wherein detection of amplified nucleic acid indicates the presence of West Nile virus in said test sample, wherein said amplifying step or said detecting step or both steps are performed with at least one oligonucleotide of the invention. Preferably, the methods of the invention are performed with a pair of oligonucleotides described above. More preferably, the methods of the invention are performed with a set of oligonucleotides described above. Most preferably, the methods of the invention are performed with the oligonucleotide set

5'-GACGTCCCAGAATTAGAGCGC-3' (SEQ ID NO: 28)

5'-ACGGGTTCACTACTACTGCATCTAGAGA (SEQ ID NO: 56)
CA-3' optionally labeled with a
detectable label, and 5'-TCCGGCTTCTCGTACTGTCT-3', or (SEQ ID NO: 29)

5'-GCCACCGGAAGTTGAGTAGA-3', (SEQ ID NO: 52)

-continued

5'-ATCACTTCGCGGCTTTGTTCACCCAGTC (SEQ ID NO: 59)
CT-3' optionally labeled with a
detectable label, and

5'-GAGACGGTTCTGAGGGCTTAC-3'. (SEQ ID NO: 53)

The invention provides other methods of detecting West Nile Virus in a test sample comprising the steps of hybridizing at least one oligonucleotide of the invention with West Nile virus nucleic acid in a test sample; and detecting hybridization of said at least one oligonucleotide of the invention with West Nile virus nucleic acid.

In preferred embodiments of the invention, the test sample comprises human blood plasma.

The invention also provides a method of identifying primers for detection of a nucleic acid sequence comprising the steps of (a) providing a nucleic acid sequence at least 1000 bases in length;

(b) dividing said nucleic acid sequence into non-overlapping segments approximately 500 bases in length starting from one end of said sequence; and (c) selecting forward and reverse primers each about 15-25 bases in length from the sequence of at least one segment and/or its complement, wherein the forward and reverse primers are selected to have non-overlapping sequences and produce an amplicon having from about 50 to 200 bases.

The invention also extends to primers identified by the aforementioned method.

Yet another aspect of the invention provides isolated oligonucleotides comprising from about 15 to about 75 contiguous bases of the sequence shown in FIG. 1 (SEQ ID NO: 1) or its complement, wherein the oligonucleotide binds with greater affinity to nucleic acid from North American or Israeli West Nile virus isolates than West Nile virus isolates originating outside North America or Israel. Preferably, the oligonucleotides comprise from about 15 to about 50 contiguous bases of the West Nile virus consensus sequence shown in FIG. 1 (SEQ ID NO: 1) or its complement. More preferably, the oligonucleotides comprise from about 15 to about 25 contiguous bases of the West Nile virus consensus sequence shown in FIG. 1 (SEQ ID NO: 1) or its complement. Still another aspect of the invention provides oligonucleotides as described above that bind with greater affinity to nucleic acid from North American or Israeli West Nile virus isolates than West Nile virus isolates originating outside the United States or Israel.

Another further aspect of the invention provides a test kit comprising at least one oligonucleotide of the invention.

These and other aspects of the invention are more fully set out in the appended claims and the following Detailed Description.

BRIEF DESCRIPTION OF THE FIGURE

FIG. 1 shows the West Nile virus consensus sequence (SEQ ID NO: 1). The consensus sequence was derived from sequence alignment and comparisons of eight approximately full-length West Nile virus genomes from isolates identified in the United States (GenBank accession numbers: AF196835, AF260967, AF202541, AF206518, AF404753, AF404754, AF404755 and AF404756) using Vector Nti Suite 7.0 (InforMax, Frederick, Md., USA).

DETAILED DESCRIPTION OF THE INVENTION

The incidence of West Nile virus infection is increasing in the United States. West Nile virus rarely kills, but about one in 150 people who become infected with the virus will develop a potentially deadly case of encephalitis or meningitis. There is no treatment or prevention of West Nile virus infection at present. Early detection is important for diagnosing infection and treating symptoms. Detection of West Nile virus in donated blood is important to the prevention of infection resulting from contaminated blood or blood derivatives.

The present invention provides methods and oligonucleotide reagents for detecting West Nile virus. The methods and oligonucleotides of the invention are especially useful for detecting West Nile virus in blood plasma.

The invention provides isolated oligonucleotides comprising $R_1$—N—$R_2$ wherein N is an oligonucleotide selected from the group consisting of

| Sequence | SEQ ID NO |
|---|---|
| 5'-CTGGATCGATGGAGAGGTGT-3' | (SEQ ID NO: 2) |
| 5'-TCCGGTCTTTCCTCCTCTTT-3' | (SEQ ID NO: 3) |
| 5'-CTACCGTCAGCGATCTCTCC-3' | (SEQ ID NO: 4) |
| 5'-TTCCTTTGCCAAATAGTCCG-3' | (SEQ ID NO: 5) |
| 5'-GACGTCGGGTCATTTGAAGT-3' | (SEQ ID NO: 6) |
| 5'-ACTGCAATTCCAACACCACA-3' | (SEQ ID NO: 7) |
| 5'-ATGTCCTGGATAACGCAAGG-3' | (SEQ ID NO: 8) |
| 5'-CTCCTCCAACTGCGAGAAAC-3' | (SEQ ID NO: 9) |
| 5'-ATCGCGCTTGGAATAGCTTA-3' | (SEQ ID NO: 10) |
| 5'-GACAGCCGTTCCAATGATCT-3' | (SEQ ID NO: 11) |
| 5'-AGGCCGGGTAGAGATTGACT-3' | (SEQ ID NO: 12) |
| 5'-CCTGCAGCACCAATCTGTTA-3' | (SEQ ID NO: 13) |
| 5'-CAGTGTTTATGGTGGCATCG-3' | (SEQ ID NO: 14) |
| 5'-GGCATCGTGATAAGCCATTT-3' | (SEQ ID NO: 15) |
| 5'-TGGCAGAGCTTGACATTGAC-3' | (SEQ ID NO: 16) |
| 5'-GCCGTTCTCTCAATCCACAT-3' | (SEQ ID NO: 17) |
| 5'-ATACTGGGGCAGTGTCAAGG-3' | (SEQ ID NO: 18) |
| 5'-TAACGTTCTTGCCAGGTTCC-3' | (SEQ ID NO: 19) |
| 5'-GGCTGAAGCACTGAGAGGAC-3' | (SEQ ID NO: 20) |
| 5'-ACAGGTTGTAGTTCGGCACC-3' | (SEQ ID NO: 21) |
| 5'-CCAGGCACTTCAGATCCATT-3' | (SEQ ID NO: 22) |
| 5'-CTAGGCACAAACCAAACCGT-3' | (SEQ ID NO: 23) |
| 5'-GATTGACGCCAGGGTGTACT-3.' | (SEQ ID NO: 24) |
| 5'-ATGTCTTCCCCATGAAGTGC-3' | (SEQ ID NO: 25) |
| 5'-CGCAGACAGACAACCAGCTA-3' | (SEQ ID NO: 26) |
| 5'-TTGACCTCAATTCTTTGCCC-3' | (SEQ ID NO: 27) |
| 5'-GACGTCCCAGAATTAGAGCGC-3' | (SEQ ID NO: 28) |
| 5'-TCCGGCTTCTCGTACTGTCT-3' | (SEQ ID NO: 29) |
| 5'-CTCTGTTTGGAACGCAACAA-3' | (SEQ ID NO: 30) |
| 5'-GCCCCACCTCTTTTTAGTCC-3' | (SEQ ID NO: 31) |
| 5'-AGTCGAGCTTCAGGCAATGT-3' | (SEQ ID NO: 32) |
| 5'-TGGTGTCTGAGTTGAGCAGG-3' | (SEQ ID NO: 33) |
| 5'-TGAGTACAGTTCGACGTGGC-3' | (SEQ ID NO: 34) |
| 5'-TTGAGAGGAGCCTGACCACT-3' | (SEQ ID NO: 35) |
| 5'-AGCTAAGGTGCTTGAGCTGC-3' | (SEQ ID NO: 36) |
| 5'-ATGACGGTTCTTCCATCAGC-3' | (SEQ ID NO: 37) |
| 5'-ACATCCAAGAGTGGAAACCG-3' | (SEQ ID NO: 38) |
| 5'-CGAGCTCTGCCTACCAATTC-3' | (SEQ ID NO: 39) |
| 5'-GCAGGAGGAGAGTGGATGAC-3' | (SEQ ID NO: 40) |
| 5'-TTCTCCACTGGGGTTTTGTC-3' | (SEQ ID NO: 41) |
| 5'-GGGTTAACAAAGGCAAACCA-3' | (SEQ ID NO: 42) |
| 5'-CCCTGACCTACAGCTTCAG-3' | (SEQ ID NO: 43) |
| 5'-TAGTTCGCCTGTGTGAGCTG-3' | (SEQ ID NO: 44) |
| 5'-TTTTAGCATATTGACAGCCCG-3' | (SEQ ID NO: 45) |
| 5'-TTGATTGGACTGAAGAGGGC-3' | (SEQ ID NO: 46) |
| 5'-GCAATTGCTGTGAACCTGAA-3' | (SEQ ID NO: 47) |
| 5'-GCTGAAGCTGTAGGTCAGGG-3' | (SEQ ID NO: 48) |
| 5'-CTGGTTGTGCAGAGCAGAAG-3' | (SEQ ID NO: 49) |
| 5'-GGAGAGTGCAGTCTGCGATA-3' | (SEQ ID NO: 50) |
| 5'-GTCTCCTCTAACCTCTAGTCC-3' | (SEQ ID NO: 51) |
| 5'-GCCACCGGAAGTTGAGTAGA-3' | (SEQ ID NO: 52) |
| 5'-GAGACGGTTCTGAGGGCTTAC-3' | (SEQ ID NO: 53) |
| 5'-TGGATTTGGTCTCACCAGCACTCGGATGTT-3' | (SEQ ID NO: 54) |
| 5'-ACATCCGCAGTGCCCAGAGAACATAATGGA-3' | (SEQ ID NO: 55) |
| 5'-ACGGGTTCACTACTACTGCATCTAGAGACA-3' | (SEQ ID NO: 56) |
| 5'-CCGGTAATGGTGTTAAACCAGGGCGAAAGGA-3' | (SEQ ID NO: 57) |
| 5'-CAGGAGGACTGGGTTAACAAAGGCAAACCA-3', and | (SEQ ID NO: 58) |
| 5'-ATCACTTCGCGGCTTTGTTCACCCAGTCCT-3'; | (SEQ ID NO: 59) |

$R_1$ is an oligonucleotide sequence of 0-20 contiguous bases of the West Nile virus consensus sequence shown in FIG. 1 (SEQ ID NO: 1) immediately upstream of the 5' end of N in the consensus sequence covalently linked to N at the 5' end, provided that when N is complementary to said consensus sequence, $R_1$ is selected from the complement of said consensus sequence; and $R_2$ is an oligonucleotide sequence of 0-20 contiguous bases of the consensus sequence immediately downstream of the 3'-end of N in the consensus sequence covalently linked to N at the 3' end, provided that when N is complementary to said consensus sequence, $R_2$ is selected from the complement of said consensus sequence.

The oligonucleotides are selected by locating N in the consensus sequence of FIG. 1 and continuing upstream in the 5' direction from the first base of N and selecting 0-20 bases immediately adjacent to the first base of N and/or continuing downstream in the 3' direction from the last base of N and selecting 0-20 contiguous bases immediately adjacent to the last base of N. If N is complementary to the consensus sequence, $R_1$ and $R_2$ are selected in the same manner from the complement of the consensus sequence. Preferably, $R_1$ and $R_2$ are independently 0-15 contiguous bases in length, more preferably 0-10 contiguous bases in length, most preferably 0-5 contiguous bases in length.

The invention also provides isolated fragments of N as defined herein wherein the fragment is 10-19 bases in length, preferably 15-19 bases in length.

The invention further provides isolated nucleotides comprising $R_1$—X—$R_2$, wherein X is at least 10 contiguous bases of N as defined herein, and $R_1$ and $R_2$ have the meanings defined herein, wherein when $R_1$ is present, $R_2$ is absent and X is selected such that the base at the 5'-end of X is the same as the base at the 5'-end of N; and when $R_2$ is present, $R_1$ is absent and X is selected such that the base at the 3'-end of X is the same as the base at the 3'-end of N. The oligonucleotides can be selected by locating N in the consensus sequence shown in FIG. 1 and selecting at least 10 contiguous bases beginning from the 5'-end and continuing for at least ten contiguous bases downstream towards the 3'end. Alternatively, the oligonucleotide can be selected by locating N in the consensus sequence shown in FIG. 1 and selecting at least ten contiguous bases beginning from the 3'-end and continuing for at least ten contiguous bases upstream towards the 5'-end. When X is selected from the 5'-end of N, $R_2$ is absent and $R_1$ is selected by continuing upstream in the 5' direction from the first base of N and selecting 0-20 bases immediately adjacent to the first base of N. When X is selected from the 3'-end of N, $R_1$ is absent and $R_2$ is selected by continuing downstream in the 3' direction from the last base of N and selecting 0-20 contiguous bases immediately adjacent to the last base of N. Preferably, $R_1$ and $R_2$ are independently 0-15 contiguous bases in length, more preferably 0-10 contiguous bases in length, most preferably 0-5 contiguous bases in length. If N is complementary to the consensus sequence, $R_1$ and $R_2$ are selected in the same manner from the complement of the consensus sequence.

Also provided are isolated oligonucleotides that have at least 80% sequence identity with an oligonucleotide having the formula $R_1$—N—$R_2$, wherein $R_1$, N and $R_2$ have the meanings defined herein, a fragment of N as defined herein, or an oligonucleotide having the formula $R_1$—X—$R_2$, wherein $R_1$, X and $R_2$ have the meanings defined herein. Sequence identity can be determined by manually aligning the sequences and calculating the percentage of sequence identity from the number of bases that are the same in both sequences or using a mathematical algorithm. Non-limiting examples of such mathematical algorithms are the algorithm of Myers and Miller (1988) CABIOS 4:11-17; the local homology algorithm of Smith et al. (1981) Adv. Appl. Math. 2:482; the homology alignment algorithm of Needleman and Wunsch (1970) J. Mol. Biol. 48:443-453; the search-for-similarity-method of Pearson and Lipman (1988) Proc. Natl. Acad. Sci. 85:2444-2448; the algorithm of Karlin and Altschul (1990) Proc. Natl. Acad. Sci. USA 87:2264, modified as in Karlin and Altschul (1993) Proc. Natl. Acad. Sci. USA 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. Preferably, the oligonucleotide has 85, 90 or 95% sequence identity with an oligonucleotide of the formula $R_1$—N—$R_2$, wherein $R_1$, N and $R_2$ have the meanings as defined herein, a fragment of N as defined herein, or an oligonucleotide having the formula $R_1$X—$R_2$ wherein $R_1$, X and $R_2$ have the meanings defined herein.

The invention further provides isolated oligonucleotides that are the full-length complement of the oligonucleotides.

The term "isolated" oligonucleotide refers to an oligonucleotide that is found in a condition other than its native environment. In a preferred form, the oligonucleotide is substantially free from other nucleic acid sequences, such as other chromosomal and extrachromosomal DNA and RNA, that normally accompany or interact with it as found in its naturally occurring environment. The term "isolated" oligonucleotide also embraces recombinant oligonucleotides and chemically synthesized oligonucleotides.

Another aspect of the invention provides methods of detecting West Nile virus in a sample suspected of containing the virus comprising the steps of amplifying West Nile Virus nucleic acid in a sample suspected of containing such virus; and detecting amplified nucleic acid, wherein detection of amplified nucleic acid indicates the presence of West Nile virus in the sample, which method uses at least one oligonucleotide of the invention to amplify or detect West Nile virus nucleic acid.

A further aspect of the invention provides methods of detecting West Nile virus in a sample comprising the steps of hybridizing at least one oligonucleotide of the invention with West Nile virus nucleic acid and detecting hybridization of the at least one oligonucleotide with the West Nile virus nucleic acid.

West Nile virus is an RNA genome virus and it will be necessary in some assay formats to convert the RNA into DNA prior to amplification. Conversion of the RNA into DNA can be done using reverse transcriptase.

The amplifying step can be performed using any type of nucleic acid template-based method, such as polymerase chain reaction (PCR) technology.

PCR technology relies on thermal strand separation followed by thermal dissociation. During this process, at least one primer per strand, cycling equipment, high reaction temperatures and specific thermostable enzymes are used (U.S. Pat. Nos. 4,683,195 and 4,883,202). Alternatively, it is possible to amplify the DNA at a constant temperature (Nucleic Acids Sequence Based Amplification (NASBA) Kievits, T., et al., J. Virol Methods, 1991; 35, 273-286; and Malek, L. T., U.S. Pat. No. 5,130,238; T7 RNA polymerase-mediated amplification (TMA) (Giachetti C, et al. J Clin Microbiol 2002 July;40(7):2408-19; or Strand Displacement Amplification (SDA), Walker, G. T. and Schram, J. L., European Patent Application Publication No. 0 500 224 A2; Walker, G. T., et al., Nuc. Acids Res., 1992; 20, 1691-1696).

Preferably, amplification is done using PCR and at least one oligonucleotide primer selected from the consensus sequence or its complement. Primers are preferably 15-30 nucleotides long, more preferably 15 to 25 bases long, most preferably, about twenty nucleotides long. Preferably, the at least one primer is an oligonucleotide selected from the group consisting of

| | |
|---|---|
| 5'-CTGGATCGATGGAGAGGTGT-3', | (SEQ ID NO: 2) |
| 5'-TCCGGTCTTTCCTCCTCTTT-3', | (SEQ ID NO: 3) |
| 5'-CTACCGTCAGCGATCTCTCC-3', | (SEQ ID NO: 4) |
| 5'-TTCCTTTGCCAAATAGTCCG-3', | (SEQ ID NO: 5) |
| 5'-GACGTCGGGTCATTTGAAGT-3', | (SEQ ID NO: 6) |
| 5'-ACTGCAATTCCAACACCACA-3', | (SEQ ID NO: 7) |
| 5'-ATGTCCTGGATAACGCAAGG-3', | (SEQ ID NO: 8) |
| 5'-CTCCTCCAACTGCGAGAAAC-3', | (SEQ ID NO: 9) |
| 5'-ATCGCGCTTGGAATAGCTTA-3', | (SEQ ID NO: 10) |
| 5'-GACAGCCGTTCCAATGATCT-3', | (SEQ ID NO: 11) |
| 5'-AGGCCGGGTAGAGATTGACT-3', | (SEQ ID NO: 12) |
| 5'-CCTGCAGCACCAATCTGTTA-3', | (SEQ ID NO: 13) |
| 5'-CAGTGTTTATGGTGGCATCG-3', | (SEQ ID NO: 14) |
| 5'-GGCATCGTGATAAGCCATTT-3', | (SEQ ID NO: 15) |
| 5'-TGGCAGAGCTTGACATTGAC-3', | (SEQ ID NO: 16) |
| 5'-GCCGTTCTCTCAATCCACAT-3', | (SEQ ID NO: 17) |
| 5'-ATACTGGGGCAGTGTCAAGG-3', | (SEQ ID NO: 18) |
| 5'-TAACGTTCTTGCCAGGTTCC-3', | (SEQ ID NO: 19) |
| 5'-GGCTGAAGCACTGAGAGGAC-3', | (SEQ ID NO: 20) |
| 5'-ACAGGTTGTAGTTCGGCACC-3', | (SEQ ID NO: 21) |
| 5'-CCAGGCACTTCAGATCCATT-3', | (SEQ ID NO: 22) |
| 5'-CTAGGCACAAACCAAACCGT-3', | (SEQ ID NO: 23) |
| 5'-GATTGACGCCAGGGTGTACT-3', | (SEQ ID NO: 24) |
| 5'-ATGTCTTCCCCATGAAGTGC-3', | (SEQ ID NO: 25) |
| 5'-CGCAGACAGACAACCAGCTA-3', | (SEQ ID NO: 26) |
| 5'-TTGACCTCAATTCTTTGCCC-3', | (SEQ ID NO: 27) |
| 5'-GACGTCCCAGAATTAGAGCGC-3', | (SEQ ID NO: 28) |
| 5'-TCCGGCTTCTCGTACTGTCT-3' | (SEQ ID NO: 29) |
| 5'-CTCTGTTTGGAACGCAACAA-3', | (SEQ ID NO: 30) |
| 5'-GCCCCACCTCTTTTTAGTCC-3', | (SEQ ID NO: 31) |
| 5'-AGTCGAGCTTCAGGCAATGT-3', | (SEQ ID NO: 32) |
| 5'-TGGTGTCTGAGTTGAGCAGG-3', | (SEQ ID NO: 33) |
| 5'-TGAGTACAGTTCGACGTGGC-3', | (SEQ ID NO: 34) |
| 5'-TTGAGAGGAGCCTGACCACT-3', | (SEQ ID NO: 35) |
| 5'-AGCTAAGGTGCTTGAGCTGC-3', | (SEQ ID NO: 36) |
| 5'-ATGACGGTTCTTCCATCAGC-3', | (SEQ ID NO: 37) |
| 5'-ACATCCAAGAGTGGAAACCG-3', | (SEQ ID NO: 38) |
| 5'-CGAGCTCTGCCTACCAATTC-3', | (SEQ ID NO: 39) |
| 5'-GCAGGAGGAGAGTGGATGAC-3', | (SEQ ID NO: 40) |
| 5'-TTCTCCACTGGGGTTTTGTC-3', | (SEQ ID NO: 41) |
| 5'-GGGTTAACAAAGGCAAACCA-3', | (SEQ ID NO: 42) |
| 5'-CCCTGACCTACAGCTTCAG-3', | (SEQ ID NO: 43) |
| 5'-TAGTTCGCCTGTGTGAGCTG-3', | (SEQ ID NO: 44) |
| 5'-TTTTAGCATATTGACAGCCCG-3', | (SEQ ID NO: 45) |
| 5'-TTGATTGGACTGAAGAGGGC-3', | (SEQ ID NO: 46) |
| 5'-GCAATTGCTGTGAACCTGAA-3', | (SEQ ID NO: 47) |
| 5'-GCTGAAGCTGTAGGTCAGGG-3', | (SEQ ID NO: 48) |
| 5'-CTGGTTGTGCAGAGCAGAAG-3', | (SEQ ID NO: 49) |
| 5'-GGAGAGTGCAGTCTGCGATA-3', | (SEQ ID NO: 50) |
| 5'-GTCTCCTCTAACCTCTAGTCC-3', | (SEQ ID NO: 51) |
| 5'-GCCACCGGAAGTTGAGTAGA-3', and | (SEQ ID NO: 52) |
| 5'-GAGACGGTTCTGAGGGCTTAC-3'. | (SEQ ID NO: 53) |

More preferably, amplification is done with a pair of oligonucleotides of the invention as primers, the pair of primers selected from the group consisting of

| | |
|---|---|
| (a) 5'-CTGGATCGATGGAGAGGTGT-3' and | (SEQ ID NO: 2) |
| 5'-TCCGGTCTTTCCTCCTCTTT-3' | (SEQ ID NO: 3) |
| (b) 5'-CTACCGTCAGCGATCTCTCC-3' and | (SEQ ID NO: 4) |
| 5'-TTCCTTTGCCAAATAGTCCG-3' | (SEQ ID NO: 5) |
| (c) 5'-GACGTCGGGTCATTTGAAGT-3' and | (SEQ ID NO: 6) |
| 5'-ACTGCAATTCCAACACCACA-3' | (SEQ ID NO: 7) |
| (d) 5'-ATGTCCTGGATAACGCAAGG-3' and | (SEQ ID NO: 8) |
| 5'-CTCCTCCAACTGCGAGAAAC-3' | (SEQ ID NO: 9) |
| (e) 5'-ATCGCGCTTGGAATAGCTTA-3' and | (SEQ ID NO: 10) |
| 5'-GACAGCCGTTCCAATGATCT-3' | (SEQ ID NO: 11) |
| (f) 5'-AGGCCGGGTAGAGATTGACT-3' and | (SEQ ID NO: 12) |
| 5'-CCTGCAGCACCAATCTGTTA-3' | (SEQ ID NO: 13) |
| (g) 5'-CAGTGTTTATGGTGGCATCG-3' and | (SEQ ID NO: 14) |
| 5'-GGCATCGTGATAAGCCATTT-3' | (SEQ ID NO: 15) |
| (h) 5'-TGGCAGAGCTTGACATTGAC-3' and | (SEQ ID NO: 16) |
| 5'-GCCGTTCTCTCAATCCACAT-3' | (SEQ ID NO: 17) |
| (i) 5'-ATACTGGGGCAGTGTCAAGG-3' and | (SEQ ID NO: 18) |
| 5'-TAACGTTCTTGCCAGGTTCC-3' | (SEQ ID NO: 19) |
| (j) 5'-GGCTGAAGCACTGAGAGGAC-3' and | (SEQ ID NO: 20) |
| 5'-ACAGGTTGTAGTTCGGCACC-3' | (SEQ ID NO: 21) |
| (k) 5'-CCAGGCACTTCAGATCCATT-3' and | (SEQ ID NO: 22) |
| 5'-CTAGGCACAAACCAAACCGT-3' | (SEQ ID NO: 23) |

(l) 5'-GATTGACGCCAGGGTGTACT-3' and (SEQ ID NO: 24)

5'-ATGTCTTCCCCATGAAGTGC-3'     (SEQ ID NO: 25)

(m) 5'-CGCAGACAGACAACCAGCTA-3' and (SEQ ID NO: 26)

5'-TTGACCTCAATTCTTTGCCC-3'     (SEQ ID NO: 27)

(n) 5'-GACGTCCCAGAATTAGAGCGC-3' and (SEQ ID NO: 28)

5'-TCCGGCTTCTCGTACTGTCT-3'     (SEQ ID NO: 29)

(o) 5'-CTCTGTTTGGAACGCAACAA-3' and (SEQ ID NO: 30)

5'-GCCCCACCTCTTTTTAGTCC-3'     (SEQ ID NO: 31)

(p) 5'-AGTCGAGCTTCAGGCAATGT-3' and (SEQ ID NO: 32)

5'-TGGTGTCTGAGTTGAGCAGG-3'     (SEQ ID NO: 33)

(q) 5'-TGAGTACAGTTCGACGTGGC-3' and (SEQ ID NO: 34)

5'-TTGAGAGGAGCCTGACCACT-3'     (SEQ ID NO: 35)

(r) 5'-AGCTAAGGTGCTTGAGCTGC-3' and (SEQ ID NO: 36)

5'-ATGACGGTTCTTCCATCAGC-3'     (SEQ ID NO: 37)

(s) 5'-ACATCCAAGAGTGGAAACCG-3' and (SEQ ID NO: 38)

5'-CGAGCTCTGCCTACCAATTC-3'     (SEQ ID NO: 39)

(t) 5'-GCAGGAGGAGAGTGGATGAC-3' and (SEQ ID NO: 40)

5'-TTCTCCACTGGGGTTTTGTC-3'     (SEQ ID NO: 41)

(u) 5'-GGGTTAACAAAGGCAAACCA-3' and (SEQ ID NO: 42)

5'-CCCTGACCTACAGCTTCAG-3'      (SEQ ID NO: 43)

(v) 5'-TAGTTCGCCTGTGTGAGCTG-3' and (SEQ ID NO: 44)

5'-TTTTAGCATATTGACAGCCCG-3'    (SEQ ID NO: 45)

(w) 5'-TTGATTGGACTGAAGAGGGC-3' and (SEQ ID NO: 46)

5'-GCAATTGCTGTGAACCTGAA-3'     (SEQ ID NO: 47)

(x) 5'-GCTGAAGCTGTAGGTCAGGG-3' and (SEQ ID NO: 48)

5'-CTGGTTGTGCAGAGCAGAAG-3'     (SEQ ID NO: 49)

(y) 5'-GGAGAGTGCAGTCTGCGATA-3' and (SEQ ID NO: 50)

5'-GTCTCCTCTAACCTCTAGTCC-3'    (SEQ ID NO: 51)

(z) 5'-GCCACCGGAAGTTGAGTAGA-3' and (SEQ ID NO: 52)

5'-GAGACGGTTCTGAGGGCTTAC-3'.   (SEQ ID NO: 53)

Most preferably amplification is done using a pair of isolated oligonucleotides selected from the group consisting of (f) 5'-ATCGCGCTTGGAATAGCTTA-3' and (SEQ ID NO: 10)

5'-GACAGCCGTTCCAATGATCT-3'     (SEQ ID NO: 11)

(j) 5'-GGCTGAAGCACTGAGAGGAC-3' and (SEQ ID NO: 20)

5'-ACAGGTTGTAGTTCGGCACC-3'     (SEQ ID NO: 21)

(n) 5'-GACGTCCCAGAATTAGAGCGC-3' and (SEQ ID NO: 28)

5'-TCCGGCTTCTCGTACTGTCT-3'     (SEQ ID NO: 29)

(u) 5'-GGGTTAACAAAGGCAAACCA-3' and (SEQ ID NO: 42)

5'-CCCTGACCTACAGCTTCAG-3'      (SEQ ID NO: 43)

(y) 5'-GGAGAGTGCAGTCTGCGATA-3' and (SEQ ID NO: 50)

5'-GTCTCCTCTAACCTCTAGTCC-3'    (SEQ ID NO: 51)

(z) 5'-GCCACCGGAAGTTGAGTAGA-3' and (SEQ ID NO: 52)

5'-GAGACGGTTCTGAGGGCTTAC-3'.   (SEQ ID NO: 53)

Especially preferred pairs of isolated oligonucleotides for amplifying West Nile virus nucleic acid are 5'-GACGTCCCAGAATTAGAGCGC-3' and (SEQ ID NO: 28)

5'-TCCGGCTTCTCGTACTGTCT-3' and  (SEQ ID NO: 29)

5'-GCCACCGGAAGTTGAGTAGA-3' and  (SEQ ID NO: 52)

5'-GAGACGGTTCTGAGGGCTTAC-3'.    (SEQ ID NO: 53)

Amplified nucleic acid can be detected using a variety of detection technologies well known in the art. For example, amplification products may be detected using agarose gel by performing electrophoresis with visualization by ethidium bromide staining and exposure to ultraviolet (UV) light, by sequence analysis of the amplification product for confirmation, or hybridization with an oligonucleotide probe.

Preferably, amplified nucleic acid is detected by hybridization with an oligonucleotide probe derived from the West Nile virus consensus sequence or its complement. Probe sequences preferably are 10 to 50 nucleotides long, more preferably 15 to 40 nucleotides long, most preferably 25-35 nucleotides long and are selected from the sequence that is amplified by a pair of primers. Probes can be optionally labeled with a detectable label.

Preferred probes include an isolated oligonucleotide selected from the group consisting of

5'-TGGATTTGGTCTCACCAGCACTCGGATG TT-3',  (SEQ ID NO: 54)

5'-ACATCCGCAGTGCCCAGAGAACATAATG GA-3',  (SEQ ID NO: 55)

5'-ACGGGTTCACTACTACTGCATCTAGAGA CA-3',  (SEQ ID NO: 56)

5'-CCGGTAATGGTGTTAAACCAGGGCGAAA GGA-3',  (SEQ ID NO: 57)

5'-CAGGAGGACTGGGTTAACAAAGGCAAAC CA-3', and  (SEQ ID NO: 58)

5'-ATCACTTCGCGGCTTTGTTCACCCAGTC CT-3'.  (SEQ ID NO: 59)

More preferably the oligonucleotide probe is

5'-ACGGGTTCACTACTACTGCATCTAGAGA CA-3', or  (SEQ ID NO: 56)

5'-ATCACTTCGCGGCTTTGTTCACCCAGTC CT-3'.  (SEQ ID NO: 59)

Preferably, the oligonucleotide probe is labeled with a detectable label. The detectable label can be any molecule or moiety having a property or characteristic that is capable of detection, such as, for example, radioisotopes, fluorophores, chemiluminophores, enzymes, colloidal particles, and fluorescent microparticles.

Probe sequences can be employed using a variety of methodologies to detect amplification products. Generally all such methods employ a step where the probe hybridizes to a strand of an amplification product to form an amplification product/probe hybrid. The hybrid can then be detected using labels on the primer, probe or both the primer and probe. Examples of homogeneous detection platforms for detecting amplification products include the use of FRET (fluorescence resonance energy transfer) labels attached to probes that emit a signal in the presence of the target sequence. "TaqMan" assays described in U.S. Pat. Nos. 5,210,015; 5,804,375; 5487,792 and 6214,979 (each of which is herein incorporated by reference) and Molecular Beacon assays described in U.S. Pat. No. 5,925,517 (herein incorporated by reference) are examples of techniques that can be employed to detect nucleic acid sequences. With the "TaqMan" assay format, products of the amplification reaction can be detected as they are formed or in a so-called "real time" manner. As a result, amplification product/probe hybrids are formed and detected while the reaction mixture is under amplification conditions.

Preferably, the PCR probes are TaqMan® probes that are labeled at the 5' end with a fluorophore and at the 3'-end with a quencher molecule. Suitable fluorophores and quenchers for use with TaqMan® probes are disclosed in U.S. Pat. Nos. 5,210,015, 5,804,375, 5,487,792 and 6,214,979 and WO 01/86001 (Biosearch Technologies). Preferred quenchers are Black Hole Quenchers disclosed in WO 01/86001.

In preferred embodiments of the invention, oligonucleotide primers are used to amplify West Nile virus nucleic acid in a test sample by PCR after reverse transcription of the West Nile virus RNA to DNA. Amplified nucleic acid is detected using a dual labeled "TaqMan" probe that is labeled with 5-carboxyfluorescein (FAM) at the 5' end and a Black Hole quencher as disclosed in WO 01/86001 at the 3' end. Fluorescence is detected using a fluorimeter.

The method of the invention is preferably performed using a set of oligonucleotides selected from the group consisting of

```
(aa) 5'-ATCGCGCTTGGAATAGCTTA-3',       (SEQ ID NO: 10)

5'-TGGATTTGGTCTCACCAGCACTCGGA     (SEQ ID NO: 54)
     TGTT-3' optionally labeled
     with a detectable label, and

5'-GACAGCCGTTCCAATGATCT-3';       (SEQ ID NO: 11)

(bb) 5'-GGCTGAAGCACTGAGAGGAC-3',       (SEQ ID NO: 20)

5'-ACATCCGCAGTGCCCAGAGAACATAA     (SEQ ID NO: 55)
     TGGA-3' optionally labeled
     with a detectable label, and

5'-ACAGGTTGTAGTTCGGCACC-3';       (SEQ ID NO: 21)

(cc) 5'-GACGTCCCAGAATTAGAGCGC-3',      (SEQ ID NO: 28)

5'-ACGGGTTCACTACTACTGCATCTAGA     (SEQ ID NO: 56)
     GACA-3' optionally labeled
     with a detectable label, and

5'-TCCGGCTTCTCGTACTGTCT-3';       (SEQ ID NO: 29)
```

```
                    -continued
(dd) 5'-GGGTTAACAAAGGCAAACCA-3',       (SEQ ID NO: 42)

5'-CCGGTAATGGTGTTAAACCAGGGCGA     (SEQ ID NO: 57)
     AAGGA-3' optionally labeled
     with a detectable label, and

5'-CCCTGACCTACAGCTTCAG-3'         (SEQ ID NO: 43)

(ee) 5'-GGAGAGTGCAGTCTGCGATA-3',       (SEQ ID NO: 50)

5'-CAGGAGGACTGGGTTAACAAAGGCAA     (SEQ ID NO: 58)
     ACCA-3' optionally labeled
     with a detectable label, and

5'-GTCTCCTCTAACCTCTAGTCC-3';      (SEQ ID NO: 51)

(ff) 5'-GCCACCGGAAGTTGAGTAGA-3',       (SEQ ID NO: 52)

5'-ATCACTTCGCGGCTTTGTTCACCCAG     (SEQ ID NO: 59)
     TCCT-3' optionally labeled
     with a detectable label, and

5'-GAGACGGTTCTGAGGGCTTAC-3'.      (SEQ ID NO: 53)
```

More preferably, the method of the invention is performed using either of the following sets of oligonucleotides

```
(cc) 5'-GACGTCCCAGAATTAGAGCGC-3',      (SEQ ID NO: 28)

5'-ACGGGTTCACTACTACTGCATCTAGA     (SEQ ID NO: 56)
     GACA-3' optionally labeled
     with a detectable label, and

5'-TCCGGCTTCTCGTACTGTCT-3';       (SEQ ID NO: 29)

(ff) 5'-GCCACCGGAAGTTGAGTAGA-3',       (SEQ ID NO: 52)

5'-ATCACTTCGCGGCTTTGTTCACCCAG     (SEQ ID NO: 59)
     TCCT-3', optionally labeled
     with a detectable label, and

5'-GAGACGGTTCTGAGGGCTTAC-3'.      (SEQ ID NO: 53)
```

In each of the foregoing sets of oligonucleotides, the first and third oligonucleotides are used as primers and the middle oligonucleotide is used as a probe for detecting amplified nucleic acid. The probe is optionally labeled with a detectable label.

The oligonucleotides of the invention can also be used to detect West Nile virus using methods and techniques that are known in the art that are not based on nucleic acid amplification.

Nucleic acid hybridization can be done using techniques and conditions known in the art. Specific hybridization conditions will depend on the type of assay in which hybridization is used. Hybridization techniques and conditions can be found, for example, in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York) and Sambrook et al. (1989) Molecular Cloning. A Laboratory Manual (2d ed., Cold Spring Harbor Laboratory Press, Plainview, N.Y.).

Hybridization of nucleic acid may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified. Alternatively, stringency conditions can be adjusted to allow some mismatching in sequences so that lower degrees of similarity are detected.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37.degree. C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5.x to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours, or less depending on the assay format.

It should be noted that the oligonucleotides of the invention can be used as primers or probes, depending on the intended use or assay format. For example, an oligonucleotide used as a primer in one assay can be used as a probe in another assay. The grouping of the oligonucleotides into primer pairs and primer/probe sets reflects certain preferred embodiments of the invention. However, the use of other primer pairs comprised of forward and reverse primers selected from different preferred primer pairs is specifically contemplated.

The term "test sample" as used herein, means anything designated for testing for the presence of West Nile virus and/or West Nile virus nucleic acid. The test sample is, or can be derived from any biological source, such as for example, blood, blood plasma, cell cultures, tissues and mosquito samples. The test sample can be used directly as obtained from the source, or following a pre-treatment to modify the character of the sample. Thus, the test sample can be pre-treated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, and purifying nucleic acid.

The oligonucleotides of the invention can be made with standard molecular biology techniques known in the art and disclosed in manuals such as Sambrook et al., *Molecular Cloning: A Laboratory Manual*, Cold Spring Harbor Laboratory Press, Cold Spring Harbor, N.Y., USA (1989) or conventional nucleotide phosphoramidite chemistry and commercially available synthesizer instruments. The oligonucleotides of the invention can be DNA or RNA. The invention is also directed to the RNA equivalents of the oligonucleotides of the invention and their complements.

Another aspect of the invention provides a method of identifying primers for detection of a nucleic acid sequence, which method comprises the steps of (a) providing a nucleic acid sequence at least 1000 bases in length; (b) dividing the nucleic acid sequence into non-overlapping segments approximately 500 bases in length starting from one end of the sequence; and (c) selecting forward and reverse primers each about 15-25 bases in length from the sequence of at least one segment and/or its complement, wherein the forward and reverse primers are selected to have non-overlapping sequences and produce an amplicon having from about 50 to 200 bases.

The method of the invention can be used for identifying primers for detection of any nucleic acid sequence at least about 1,000 bases in length, including the entire genome of an organism such as a virus. Unlike prior methods where portions of a known gene or other location in the sequence were used to identify primers, the method of the invention systematically covers the entire sequence without regard to open reading frames or other landmarks in the sequence. The method can be used with any type of sequence including native or consensus sequences. The nucleic acid sequence is divided into non-overlapping segments approximately 500 bases long. For sequences that are not multiples of 500, the length of the segments can be adjusted to take into account additional bases, or the additional bases at the end can be used as a shorter segment. One or more sets of primers are selected from at least one segment and/or its complement, preferably using primer design software such as 3 Primer 3 PCR primer design software (Whitehead Institute for Biomedical Research, Cambridge, Mass.). Preferably, one or more sets of primers are selected from each of the segments. Primer design takes generally takes into account factors such as primer length, melting temperature ($T_m$), specificity, complementary primer sequences, G/C content, polypyrimidine (T,C) or polypurine (A,G) stretches, and the assay format and conditions under which the primers will be used. The primer sets can be tested for their ability to amplify the segment from which they were selected using the same assay format and conditions.

With regard to the West Nile virus, a 10944 bp region of the consensus sequence in FIG. 1 that showed the highest sequence conservation from the eight full-length US WNV isolates was selected for PCR amplification primer design. This region of homology was systematically broken into approximately 500 bp sections, and within each section 1 pair of amplification primers were selected using Primer 3 PCR primer design software (Whitehead Institute for Biomedical Research, Cambridge, Mass.). Default settings for primer design using Primer 3 were optimized for 100-150 bp amplicons, primer $T_m$ (melting temperature) in the 55-60° C. range, and G/C content optimized for dual-labeled fluorescent probe-based assays ("TaqMan" assays).

Another aspect of the invention provides methods for detecting West Nile virus in a test sample comprising the steps of amplifying West Nile Virus nucleic acid in said test sample; and detecting amplified nucleic acid, wherein detection of amplified nucleic acid indicates the presence of West Nile virus in said test sample, wherein the method uses at least one oligonucleotide identified according to the method discussed above to amplify or detect West Nile virus nucleic acid.

Utilization of the West Nile virus consensus sequence shown in FIG. 1 for selection of primers and probes resulted in identification of oligonucleotides with higher sequence homology to North American or Israeli West Nile virus isolates than West Nile virus infections originating outside North America or Israel.

An additional aspect of the invention thus provides an isolated oligonucleotide comprising from about 15 to about 75 contiguous bases of the consensus sequence or its complement, more preferably from about 15 to about 60 contiguous bases, most preferably from about 15 to about 30 continuous bases of the consensus sequence or its complement, wherein the oligonucleotide bonds with greater affinity to nucleic acid from North American or Israeli West Nile virus isolates than West Nile virus isolates originating outside North America or Israel.

Lanciotti et al., Virology, 298: 96-105, 2002 discloses a phylogenetic analysis of West Nile Virus Strains isolated from the United States, Europe and the Middle East. The phylogenietic trees constructed by Lanciotti et al. revealed the presence of two genetic lineages of West Nile viruses. Lineage 1 West Nile viruses have been isolated from the northeastern United States, Europe, Israel, Africa, India, Russia and Australia. Lineage 2 West Nile viruses have been isolated only in sub-Saharan Africa and Madagascar. The lineage 1 viruses were further subdivided into three monophyletic clades. All of the isolates originating from the United States and Israel were found to be closely related to each other and were placed into the same lade, referred to as the US/Israel clade. Accession numbers for the American isolates used for phylogenetic analysis by Lanciotti et al. and by the Applicants for construction of the consensus sequence of FIG. 1 are in Example 1. The accession number of the isolate from an Israeli stork is GeneBank accession no. AY033389. Lanciotti et al. found that isolates from the United States and Israel had greater than 99% nucleotide sequence identity and amino acid identity. Isolates originating from other parts of the world had less nucleotide sequence identity (96.5% or less with the U.S. and Israeli isolates, but in many cases the amino acid sequence identity was still greater than 99%.

The invention further provides test kits comprising at least one oligonucleotide of the invention. Often, test kits contain one or more pairs of oligonucleotides such as the primer pairs disclosed herein, or one or more oligonucleotide sets as disclosed herein. The assay kit can further comprise the four-deoxynucleotide phosphates (dATP, dGTP, dCTP, dTTP) and an effective amount of a nucleic acid polymerizing enzyme. A number of enzymes are known in the art which are useful as polymerizing agents. These include, but are not limited to *E. coli* DNA polymerase I, Klenow fragment, bacteriophage T7 RNA polymerase, reverse transcriptase, and polymerases derived from thermophilic bacteria, such as *Thermus aquaticus*. The latter polymerases are known for their high temperature stability, and include, for example, the Taq DNA polymerase I. Other enzymes such as Ribonuclease H can be included in the assay kit for regenerating the template DNA. Other optional additional components of the kit include, for example, means used to label the probe and/or primer (such as a fluorophore, quencher, chromogen, etc.), and the appropriate buffers for reverse transcription, PCR, or hybridization reactions. Usually, the kit also contains instructions for carrying out the methods.

EXAMPLES

Example 1

West Nile Virus (WNV) Sequence Analysis: Consensus Sequence

WNV has a single strand positive-polarity RNA genome of approximately 11 kb. GenBank searches resulted in the identification of eight approximately full-length WNV genome sequences from isolates identified in the United States (GenBank accession numbers: AF196835, AF260967, AF202541, AF206518, AF404753, AF404754, AF404755 and AF404756). Sequence alignment and comparisons were performed using Vector Nti Suite 7.0 (InforMax, Frederick, Md., USA) and a consensus sequence was derived from the analysis of these eight sequences (entire WNV consensus sequence is listed in FIG. 1). The currently known US isolates of WNV have high homology at the nucleotide level, most likely the result of a recent "founder effect" infection of the virus in the US. WNV sequence comparison to European and other more ancestral isolates to the US strains reveals a much higher diversity at the nucleotide level.

Example 2

2.1 PCR Amplification Primer Design:

From the WNV consensus sequence, a 10944 bp region of highest sequence conservation from the eight full-length US WNV isolates was selected for PCR amplification primer design. This region of homology was systematically broken into 500 bp sections, and within each section 1 pair of amplification primers were selected using Primer 3 PCR primer design software (Whitehead Institute for Biomedical Research, Cambridge, Mass.). Default settings for primer design using Primer 3 were optimized for 100-150 bp amplicons, primer $T_m$ (melting temperature) in the 55-60° C. range, and G/C content optimized for dual-labeled fluorescent probe-based assays (Applied Biosystems, Foster City, Calif.).

Primer sequences identified for WNV amplification were chemically synthesized. Each of the individual amplification primer pairs were assayed for the ability to amplify WNV RNA using reverse transcription and polymerase chain reaction (RT-PCR; Brilliant™ Plus Single Step QRT-PCR system, Stratagene, La Jolla, Calif., USA). Reactions were setup using each of the thirty-one WNV amplification primer pairs along with a no template negative PCR control. After RT-PCR reactions were completed, 5 μL of the total 50 μL reaction volume was used for electrophoresis on a 4-20% polyacrylamide gel to determine if the RT-PCR had been successful. PCR amplicons of the predicted size were observed in 28 of 31 reactions performed.

Primers, excluding the primer pairs that produced no amplicon, are shown in Table 1.

TABLE 1

| | | |
|---|---|---|
| (a) | WNVamp1F 5'-CTGGATCGATGGAGAGGTGT-3' | (SEQ ID NO: 2) |
| | WNVamp1R 5'-TCCGGTCTTTCCTCCTCTTT-3' | (SEQ ID NO: 3) |
| (b) | WNVamp3F 5'-CTACCGTCAGCGATCTCTCC-3' | (SEQ ID NO: 4) |
| | WNVamp3R 5'-TTCCTTTGCCAAATAGTCCG-3' | (SEQ ID NO: 5) |
| (c) | WNVamp4F 5'-GACGTCGGGTCATTTGAAGT-3' | (SEQ ID NO: 6) |
| | WNVamp4R 5'-ACTGCAATTCCAACACCACA-3' | (SEQ ID NO: 7) |
| (d) | WNVamp5F 5'-ATGTCCTGGATAACGCAAGG-3' | (SEQ ID NO: 8) |
| | WNVamp5R 5'-CTCCTCCAACTGCGAGAAAC-3' | (SEQ ID NO: 9) |
| (e) | WNVamp6F 5'-ATCGCGCTTGGAATAGCTTA-3' | (SEQ ID NO: 10) |
| | WNVamp6R 5'-GACAGCCGTTCCAATGATCT-3' | (SEQ ID NO: 11) |

TABLE 1-continued

| | | | |
|---|---|---|---|
| (f) | WNVamp7F  5'-AGGCCGGGTAGAGATTGACT-3' | (SEQ ID NO: 12) |
| | WNVamp7R  5'-CCTGCAGCACCAATCTGTTA-3' | (SEQ ID NO: 13) |
| (g) | WNVamp8F  5'-CAGTGTTTATGGTGGCATCG-3' | (SEQ ID NO: 14) |
| | WNVamp8R  5'-GGCATCGTGATAAGCCATTT-3' | (SEQ ID NO: 15) |
| (h) | WNVamp9F  5'-TGGCAGAGCTTGACATTGAC-3' | (SEQ ID NO: 16) |
| | WNVamp9R  5'-GCCGTTCTCTCAATCCACAT-3' | (SEQ ID NO: 17) |
| (i) | WNVamp10F  5'-ATACTGGGGCAGTGTCAAGG-3' | (SEQ ID NO: 18) |
| | WNVamp10R  5'-TAACGTTCTTGCCAGGTTCC-3' | (SEQ ID NO: 19) |
| (j) | WNVamp11F  5'-GGCTGAAGCACTGAGAGGAC-3' | (SEQ ID NO: 20) |
| | WNVamp11R  5'-ACAGGTTGTAGTTCGGCACC-3' | (SEQ ID NO: 21) |
| (k) | WNVamp12F  5'-CCAGGCACTTCAGATCCATT-3' | (SEQ ID NO: 22) |
| | WNVamp12R  5'-CTAGGCACAAACCAAACCGT-3' | (SEQ ID NO: 23) |
| (l) | WNVamp13F  5'-GATTGACGCCAGGGTGTACT-3' | (SEQ ID NO: 24) |
| | WNVamp13R  5'-ATGTCTTCCCCATGAAGTGC-3' | (SEQ ID NO: 25) |
| (m) | WNVamp14F  5'-CGCAGACAGACAACCAGCTA-3' | (SEQ ID NO: 26) |
| | WNVamp14R  5'-TTGACCTCAATTCTTTGCCC-3' | (SEQ ID NO: 27) |
| (n) | WNVamp15F (2)  5'-GACGTCCCAGAATTAGAGCGC-3' | (SEQ ID NO: 28) |
| | WNVamp15R (2)  5'-TCCGGCTTCTCGTACTGTCT-3' | (SEQ ID NO: 29) |
| (o) | WNVamp16F  5'-CTCTGTTTGGAACGCAACAA-3' | (SEQ ID NO: 30) |
| | WNVamp16R  5'-GCCCCACCTCTTTTTAGTCC-3' | (SEQ ID NO: 31) |
| (p) | WNVamp17F  5'-AGTCGAGCTTCAGGCAATGT-3' | (SEQ ID NO: 32) |
| | WNVamp17R  5'-TGGTGTCTGAGTTGAGCAGG-3' | (SEQ ID NO: 33) |
| (q) | WNVamp18F  5'-TGAGTACAGTTCGACGTGGC-3' | (SEQ ID NO: 34) |
| | WNVamp18R  5'-TTGAGAGGAGCCTGACCACT-3' | (SEQ ID NO: 35) |
| (r) | WNVamp19F  5'-AGCTAAGGTGCTTGAGCTGC-3' | (SEQ ID NO: 36) |
| | WNVamp19R  5'-ATGACGGTTCTTCCATCAGC-3' | (SEQ ID NO: 37) |

TABLE 1-continued

| | | | |
|---|---|---|---|
| (s) | WNVamp20F  5'-ACATCCAAGAGTGGAAACCG-3' | (SEQ ID NO: 38) |
| | WNVamp20R  5'-CGAGCTCTGCCTACCAATTC-3' | (SEQ ID NO: 39) |
| (t) | WNVamp21F  5'-GCAGGAGGAGAGTGGATGAC-3' | (SEQ ID NO: 40) |
| | WNVamp21R  5'-TTCTCCACTGGGGTTTTGTC-3' | (SEQ ID NO: 41) |
| (u) | WNVamp22F  5'-GGGTTAACAAAGGCAAACCA-3' | (SEQ ID NO: 42) |
| | WNVamp22R  5'-CCCTGACCTACAGCTTCAG-3' | (SEQ ID NO: 43) |
| (v) | WNVamp23A-F  5'-TAGTTCGCCTGTGTGAGCTG-3' | (SEQ ID NO: 44) |
| | WNVamp23A-R  5'-TTTTAGCATATTGACAGCCCG-3' | (SEQ ID NO: 45) |
| (w) | WNVamp23C-F  5'-TTGATTGGACTGAAGAGGGC-3' | (SEQ ID NO: 46) |
| | WNVamp23C-R  5'-GCAATTGCTGTGAACCTGAA-3' | (SEQ ID NO: 47) |
| (x) | WNVamp24A-F  5'-GCTGAAGCTGTAGGTCAGGG-3' | (SEQ ID NO: 48) |
| | WNVamp24A-R  5'-CTGGTTGTGCAGAGCAGAAG-3' | (SEQ ID NO: 49) |
| (y) | WNVamp24B-F  5'-GGAGAGTGCAGTCTGCGATA-3' | (SEQ ID NO: 50) |
| | WNVamp24B-R  5'-GTCTCCTCTAACCTCTAGTCC-3' | (SEQ ID NO: 51) |
| (z) | WNVamp24C-F  5'-GCCACCGGAAGTTGAGTAGA-3' | (SEQ ID NO: 52) |
| | WNVamp24C-R  5'-GAGACGGTTCTGAGGGCTTAC-3' | (SEQ ID NO: 53) |

2.2 Probe Design for Fluorescence-Based PCR Detection of WNV:

Of the twenty-eight positive PCR amplification primer pairs identified within the consensus sequence of the WNV genome (FIG. 1), six sets were chosen for consideration in development of fluorescent detection of nucleic acid based on the ability to amplify WNV target at low concentrations in solution (Table 2). For this purpose, the sequences of these six WNV amplicons were evaluated using Primer-Quest[SM] software (Integrated DNA Technologies, Coralville, Iowa, USA) to identify optimal fluorescent probes that would hybridize within the WNV amplicon. Default settings for running the software were optimum probe size=30 nt; optimum probe Tm=70° C.; and optimum probe GC %=50. Probe positioning was prioritized to be within a maximum of 20 nucleotides 3' of the amplification primer, and both strands were analyzed to identify the single optimal probe that could be identified within each of the six WNV amplicons. Probes selected are shown in Table 2.

Fluorescent WNV probes containing 5-carboxyfluorescein (FAM) at the 5' end and a Black Hole Quencher (Bhquencher; BioSearch Technologies, Novato, Calif., USA) at the 3' end were synthesized. Each of the six amplification primer pair/fluorescent probe combinations (which are shown in Table 2) were tested by RT-PCR (Brilliant™ Plus Single Step QRT-PCR system, Stratagene, La Jolla, Calif., USA), for detection of WNV in diluted concentrations of target in normal human plasma (NHP). Target was diluted 1:20, 1:100, 1:200, 1:1,000, 1:2,000 and 1:10,000. All six amplification primer pair/fluorescent probe combinations were capable of detecting WNV in human plasma.

TABLE 2

| | | |
|---|---|---|
| (e) | WNVamp6F<br>5'-ATCGCGCTTGGAATAGCTTA-3' | (SEQ ID NO: 10) |
| | WNVamp6 Probe<br>5'FAM-TGGATTTGGTCTCACCAGCACTCGG ATGTT-3'BHquencher | (SEQ ID NO: 54) |
| | WNVamp6R<br>5'-GACAGCCGTTCCAATGATCT-3' | (SEQ ID NO: 11) |
| (j) | WNVamp11F<br>5'-GGCTGAAGCACTGAGAGGAC-3' | (SEQ ID NO: 20) |
| | WNVamp11 Probe<br>5'FAM-ACATCCGCAGTGCCCAGAGAACATA ATGGA-3'BHquencher | (SEQ ID NO: 55) |
| | WNVamp11R<br>5'-ACAGGTTGTAGTTCGGCACC-3' | (SEQ ID NO: 21) |
| (n) | WNVamp15F (2)<br>5'-TCCCAGAATTAGAGCGCGCGC-3' | (SEQ ID NO: 28) |
| | WNVamp15 ProbeR<br>5'FAM-ACGGGTTCACTACTACTGCATCTAG AGACA-3'BHquencher | (SEQ ID NO: 56) |
| | WNVamp15R (2)<br>5'-TCGGTCCGGCTTCTCGTACT-3' | (SEQ ID NO: 29) |
| (u) | WNVamp22F<br>5'-GGGTTAACAAAGGCAAACCA-3' | (SEQ ID NO: 42) |
| | WNVamp22 Probe<br>5'FAM-CCGGTAATGGTGTTAAACCAGGGCG AAAGGA-3'BHquencher | (SEQ ID NO: 57) |
| | WNVamp22R<br>5'-CCCTGACCTACAGCTTCAG-3' | (SEQ ID NO: 43) |

TABLE 2-continued

| | | |
|---|---|---|
| (y) | WNVamp24B-F<br>5'-GGAGAGTGCAGTCTGCGATA-3' | (SEQ ID NO: 50) |
| | WNVamp24B Probe<br>5'FAM-CAGGAGGACTGGGTTAACAAAGGCA AACCA-3'BHquencher | (SEQ ID NO: 58) |
| | WNVamp24B-R<br>5'-GTCTCCTCTAACCTCTAGTCC-3' | (SEQ ID NO: 51) |
| (z) | WNVamp24C-F<br>5'-GCCACCGGAAGTTGAGTAGA-3' | (SEQ ID NO: 52) |
| | WNVamp24C Probe<br>5'FAM-ATCACTTCGCGGCTTTGTTCACCCA GTCCT-3'BHquencher | (SEQ ID NO: 59) |
| | WNVamp24C-R<br>5'-GAGACGGTTCTGAGGGCTTAC-3' | (SEQ ID NO: 53) |

Example 3

3.1 Optimization of WNV Nucleic Acid Isolation from Human Plasma:

Nucleic acid isolations were performed on normal human plasma that had been spiked with known concentrations of WNV RNA using a Guanidine isothyocyanate lysis/alcohol precipitation procedure (AmpliScreen™ Multiprep Specimen Processing Procedure, Roche Diagnostics, Basel, Switzerland). A polyacrylamide carrier was added prior to isopropanol precipitation of RNA. One-mL volumes of plasma were utilized per isolation, and precipitated nucleic acid was suspended in elution buffer in a total volume of 200 µL. 25% of the total isolation volume (50 µL) was utilized for each RT-PCR reaction.

3.2 Optimization of RT-PCR Conditions for the Detection of WNV from Human Plasma:

The Brilliant™ Plus Single Step QRT-PCR system (Stratagene, La Jolla, Calif., USA) with minor modifications from the vendor's recommendations was utilized for nucleic acid amplification. Bovine serum albumin (BSA) was added to RT-PCR reactions. Real-time PCR was performed on an ABI7900HT DNA Detection System (Applied Biosystems, Foster City, Calif., USA). RT-PCR thermal-cycling conditions utilized were: 45° C. for 30 minutes; 95° C. for 8 minutes; then 60 cycles alternating between 95° C. for 15 seconds and 55° C. for 1 minute.

What is claimed is:

1. An isolated oligonucleotide consisting of
   (a) $R_1$-N-$R_2$ wherein
   N is an oligonucleotide selected from the group consisting of 5'-ATCGCGCTTGGAATAGCTTA-3' (SEQ ID NO: 10),
5'-GACAGCCGTTCCAATGATCT-3' (SEQ ID NO: 11),
5'-GACGTCCCAGAATTAGAGCGC-3' (SEQ ID NO: 28),
5'-TCCGGCTTCTCGTACTGTCT-3' (SEQ ID NO: 29),
5'-GCCACCGGAAGTTGAGTAGA-3' (SEQ ID NO: 52),
5'-GAGACGGTTCTGAGGGCTTAC-3' (SEQ ID NO: 53),
5'-TGGATTTGGTCTCACCAGCACTCGGATGTT-3' (SEQ ID NO: 54),
5'-ACGGGTTCACTACTACTGCATCTAGAGACA-3' (SEQ ID NO: 56),
5'-CAGGAGGACTGGGTTAACAAAGGCAAACCA-3' (SEQ ID NO: 58), and
5'-ATCACTTCGCGGCTTTGTTCACCCAGTCCT-3' (SEQ ID NO: 59);

R₁ is an oligonucleotide sequence of 0-20 contiguous bases of the West Nile virus consensus sequence shown in FIG. 1 (SEQ ID NO:1) immediately upstream of the 5' end of N in said consensus sequence covalently linked to N at the 5' end, provided that when N is complementary to said consensus sequence, R₁ is selected from the sequence complementary to said consensus sequence; and R₂ is an oligonucleotide sequence of 0-20 contiguous bases of said consensus sequence immediately downstream of the 3'-end of N in said consensus sequence covalently linked to N at the 3' end, provided that when N is complementary to said consensus sequence, R₂ is selected from the sequence complementary to said consensus sequence;

(b) an isolated fragment of N as defined in (a) wherein said fragment is 10-19 contiguous bases in length;

(c) R₁-X-R₂, wherein X is at least 10 contiguous bases of N as defined in (a), and R₁ and R₂ are as defined in (a), wherein when R₁ is present, R₂ is absent and X is selected such that the base at the 5'-end of X is the same as the base at the 5'-end of N; and when R₂ is present, R₁ is absent and X is selected such that the base at the 3'-end of X is the same as the base at the 3'-end of N;

(d) an isolated oligonucleotide 10 to 71 bases in length which has at least 90% sequence identity with an oligonucleotide of (a), (b) or (c) and binds to SEQ ID NO: 1 or its complementary sequence under stringent conditions; or (e) an isolated oligonucleotide which is the full-length complementary sequence of (a), (b), (c) or (d).

2. The oligonucleotide of claim 1 wherein said oligonucleotide consists of an oligonucleotide selected from the group consisting of 5'-ATCGCGCTTGGAATAGCTTA-3' (SEQ ID NO: 10),
5'-GACAGCCGTTCCAATGATCT-3' (SEQ ID NO: 11),
5'-GACGTCCCAGAATTAGAGCGC-3' (SEQ ID NO: 28),
5'-TCCGGCTTCTCGTACTGTCT-3' (SEQ ID NO: 29),
5'-GCCACCGGAAGTTGAGTAGA-3' (SEQ ID NO: 52), and
5'-GAGACGGTTCTGAGGGCTTAC-3' (SEQ ID NO: 53).

3. The oligonucleotide of claim 2 wherein said oligonucleotide consists of an oligonucleotide selected from the group consisting of 5'-GACGTCCCAGAATTAGAGCGC-3' (SEQ ID NO: 28),
5'-TCCGGCTTCTCGTACTGTCT-3' (SEQ ID NO: 29),
5'-GCCACCGGAAGTTGAGTAGA-3' (SEQ ID NO:52, and
5'-GAGACGGTTCTGAGGGCTTAC-3' (SEQ ID NO:53).

4. The oligonucleotide of claim 1 wherein said oligonucleotide consists of an oligonucleotide selected from the group consisting of 5'-TGGATTTGGTCTCACCAGCACTCGGATGTT-3' (SEQ ID NO: 54),
5'-ACGGGTTCACTACTACTGCATCTAGAGACA-3' (SEQ ID NO: 56),
5'-CAGGAGGACTGGGTTAACAAAGGCAAACCA-3' (SEQ ID NO: 58), and
5'-ATCACTTCGCGGCTTTGTTCACCCAGTCCT-3' (SEQ ID NO: 59).

5. The oligonucleotide of claim 4 wherein said oligonucleotide consists of 5'-ACGGGTTCACTACTACTGCATCTAGAGACA-3' (SEQ ID NO: 56), or
5'-ATCACTTCGCGGCTTTGTTCACCCAGTCCT-3' (SEQ ID NO: 59).

6. The oligonucleotide of claim 4 wherein said oligonucleotide further comprises a detectable label.

7. The oligonucleotide of claim 6 wherein said detectable label is a fluorescent molecule attached at the 5' end.

8. The oligonucleotide of claim 7 further comprising a quencher molecule attached at the 3' end.

9. A pair of isolated oligonucleotide sequences selected from the group consisting of (e) 5'-ATCGCGCTTGGAATAGCTTA-3' and (SEQ ID NO: 10)
    5'-GACAGCCGTTCCAATGATCT-3' (SEQ ID NO: 11)
(n) 5'-GACGTCCCAGAATTAGAGCGC-3' and (SEQ ID NO: 28)
    5'-TCCGGCTTCTCGTACTGTCT-3' and (SEQ ID NO: 29)
(z) 5'-GCCACCGGAAGTTGAGTAGA-3' and (SEQ ID NO: 52)
    5'-GAGACGGTTCTGAGGGCTTAC-3'. (SEQ ID NO: 53)

10. The pair of isolated oligonucleotide sequences of claim 9 wherein said pair is 5'-GACGTCCCAGAATTAGAGCGC-3' and (SEQ ID NO: 28)
5'-TCCGGCTTCTCGTACTGTCT-3'. (SEQ ID NO: 29)

11. The pair of isolated oligonucleotide sequences of claim 9 wherein said pair is 5'-GCCACCGGAAGTTGAGTAGA-3' and (SEQ ID NO: 52)
5'-GAGACGGTTCTGAGGGCTTAC-3'. (SEQ ID NO: 53)

12. A set of oligonucleotides selected from the group consisting of (aa) 5'-ATCGCGCTTGGAATAGCTTA-3', (SEQ ID NO: 10)
     5'-TGGATTTGGTCTCACCAGCACTCGGA (SEQ ID NO: 54)
     TGTT-3' optionally labeled
     with a detectable label, and
     5'-GACAGCCGTTCCAATGATCT-3'; (SEQ ID NO: 11)
(cc) 5'-GACGTCCCAGAATTAGAGCGC-3', (SEQ ID NO: 28)
     5'-ACGGGTTCACTACTACTGCATCTAGA (SEQ ID NO: 56)
     GACA-3' optionally labeled
     with a detectable label, and
     5'-GCCACCGGAAGTTGAGTAGA-3', (SEQ ID NO: 52)
(ff) 5'-ATCACTTCGCGGCTTTGTTCACCCAG (SEQ ID NO: 59)
     TCCT-3' optionally labeled
     with a detectable label, and
     5'-GAGACGGTTCTGAGGGCTTAC-3'. (SEQ ID NO: 53)

13. The set of claim 12 wherein said set is

```
(cc)  5'-GACGTCCCAGAATTAGAGCGC-3',      (SEQ ID NO: 28)

5'-ACGGGTTCACTACTACTGCATCTAGA     (SEQ ID NO: 56)
      GACA-3' optionally labeled
      with a detectable label, and

5'-TCCGGCTTCTCGTACTGTCT-3'.       (SEQ ID NO: 29)
```

14. The set of claim 12 wherein said set is

```
(ff)  5'-GCCACCGGAAGTTGAGTAGA-3',       (SEQ ID NO: 52)

5'-ATCACTTCGCGGCTTTGTTCACCCAG     (SEQ ID NO: 59)
      TCCT-3' optionally labeled
      with a detectable label, and

5'-GAGACGGTTCTGAGGGCTTAC-3'.      (SEQ ID NO: 53)
```

15. A method of detecting West Nile virus in a test sample comprising the steps of
amplifying West Nile Virus nucleic acid in said test sample; and
detecting amplified nucleic acid, wherein detection of amplified nucleic acid indicates the presence of West Nile virus in said test sample, wherein said method uses at least one oligonucleotide of claim 1 to amplify or detect West Nile virus nucleic acid.

16. A method of detecting West Nile Virus in a test sample comprising the steps of:
amplifying West Nile Virus nucleic acid in a test sample using at least one oligonucleotide of claim 2; and
detecting amplified nucleic acid, wherein detection of amplified nucleic acid indicates the presence of West Nile virus in said test sample.

17. A method of detecting West Nile Virus in a test sample comprising the steps of:
amplifying West Nile Virus nucleic acid in said test sample; and
detecting amplified nucleic acid using an oligonucleotide of claim 4, wherein detection of amplified nucleic acid indicates the presence of West Nile virus in said test sample.

18. A method of detecting West Nile Virus in a test sample comprising the steps of:
amplifying West Nile Virus nucleic acid in said test sample containing such virus using a pair of oligonucleotides of claim 9; and
detecting amplified nucleic acid, where in detection of amplified nucleic acid indicates the presence of West Nile virus in said test sample.

19. A method of detecting West Nile Virus in a test sample comprising the steps of:
amplifying West Nile Virus nucleic acid in said test sample; and
detecting amplified nucleic acid, wherein detection of amplified nucleic acid indicates the presence of West Nile virus in said test sample, wherein said amplifying step and said detecting step are performed with a set of claim 12.

20. The method of claim 19 wherein said amplifying step and said detecting step are performed with the oligonucleotide set

```
5'-TCCGGCTTCTCGTACTGTCT-3',         (SEQ ID NO: 28)

5'-ACGGGTTCACTACTACTGCATCTAGAGA     (SEQ ID NO: 56)
CA-3' optionally labeled with
a detectable label, and

5'-TCCGGCTTCTCGTACTGTCT-3'.         (SEQ ID NO: 29)
```

21. The method of claim 19 wherein said amplifying step and said detecting step are performed with the oligonucleotide set

```
5'-GCCACCGGAAGTTGAGTAGA-3',         (SEQ ID NO: 52)

5'-ATCACTTCGCGGCTTTGTTCACCCAGTC     (SEQ ID NO: 59)
CT-3' optionally labeled with
a detectable label, and

5'-GAGACGGTTCTGAGGGCTTAC-3'.        (SEQ ID NO: 53)
```

22. A method of detecting West Nile Virus in a test sample comprising the steps of
hybridizing at least one oligonucleotide of claim 1 with West Nile virus nucleic acid in a test sample; and
detecting hybridization of said at least one oligonucleotide of claim 1 with West Nile virus nucleic acid.

23. The method of any one of claims 15-22 wherein said test sample comprises human blood plasma.

24. A test kit comprising at least one oligonucleotide of claim 1.

* * * * *

SEQUENCE LISTING

```
<160> NUMBER OF SEQ ID NOS: 59

<210> SEQ ID NO 1
<211> LENGTH: 11029
<212> TYPE: DNA
<213> ORGANISM: Artificial
<220> FEATURE:
<223> OTHER INFORMATION: West Nile virus consensus sequence

<400> SEQUENCE: 1
agtagttcgc ctgtgtgagc tgacaaactt agtagtgttt gtgaggatta acaacaatta      60
acacagtgcg agctgtttct tagcacgaag atctcgatgt ctaagaaacc aggagggccc     120
ggcaagagcc gggctgtcaa tatgctaaaa cgcggaatgc cccgcgtgtt gtccttgatt     180
```

```
ggactgaaga gggctatgtt gagcctgatc gacggcaagg ggccaatacg atttgtgttg    240
gctctcttgg cgttcttcag gttcacagca attgctccga cccgagcagt gctggatcga    300
tggagaggtg tgaacaaaca aacagcgatg aaacaccttc tgagttttaa gaaggaacta    360
gggaccttga ccagtgctat caatcggcgg agctcaaaac aaaagaaaag aggaggaaag    420
accggaattg cagtcatgat tggcctgatc gccagcgtag gagcagttac cctctctaac    480
ttccaaggga aggtgatgat gacggtaaat gctactgacg tcacagatgt catcacgatt    540
ccaacagctg ctggaaagaa cctatgcatt gtcagagcaa tggatgtggg atacatgtgc    600
gatgatacta tcacttatga atgcccagtg ctgtcggctg gtaatgatcc agaagacatc    660
gactgttggt gcacaaagtc agcagtctac gtcaggtatg aagatgcac  caagacacgc    720 cactcaagac gcagtcggag gtcactgaca gtgcagacac acgagaaag  cactctagcg    780 aacaagaagg gggcttggat ggacagcacc aaggccacaa ggtatttggt aaaaacagaa    840
tcatggatct tgaggaaccc tggatatgcc ctggtggcag ccgtcattgg ttggatgctt    900
gggagcaaca ccatgcagag agttgtgttt gtcgtgctat tgcttttggt ggccccagct    960
tacagcttca actgccttgg aatgagcaac agagacttct ggaaggagt  gtctggagca   1020 acatgggtgg atttggttct cgaaggcgac agctgcgtga ctatcatgtc taaggacaag   1080
cctaccatcg atgtgaagat gatgaatatg gaggcggcca acctggcaga ggtccgcagt   1140
tattgctatt tggctaccgt cagcgatctc tccaccaaag ctgcgtgccc gaccatggga   1200
gaagctcaca atgacaaacg tgctgaccca gcttttgtgt gcagacaagg agtggtggac   1260
aggggctggg gcaacggctg cggactattt ggcaaaggaa gcattgacac atgcgccaaa   1320
tttgcctgct ctaccaaggc aataggaaga accatcttga agagaatat  caagtacgaa   1380 gtggccattt ttgtccatgg accaactact gtggagtcgc acggaaacta ctccacacag   1440
gttgagccca tcaggcagg  gagattcagc atcactcctg cggcgccttc atacacacta   1500
aagcttggag aatatggaga ggtgacagtg gactgtgaac cacggtcagg gattgacacc   1560
aatgcatact acgtgatgac tgttggaaca aagacgttct tggtccatcg tgagtggttc   1620
atggacctca acctcccttg gagcagtgct ggaagtactg tgtggaggaa cagagagacg   1680
ttaatggagt tgaggaacc  acacgccacg aagcagtctg tgatagcatt gggctcacaa   1740
gagggagctc tgcatcaagc tttggctgga gccattcctg tggaattttc aagcaacact   1800
gtcaagttga cgtcgggtca tttgaagtgt agagtgaaga tggaaaaatt gcagttgaag   1860
ggaacaacct atggcgtctg ttcaaggctt ttcaagtttc ttgggactcc cgcagacaca   1920
ggtcacggca ctgtggtgtt ggaattgcag tacactggca cggatggacc ttgcaaagtt   1980
cctatctcgt cagtggcttc attgaacgac ctaacgccag tggcagatt  ggtcactgtc   2040 aacccttttg tttcagtggc cacggccaac gctaaggtcc tgattgaatt ggaaccaccc   2100 tttgagact  catacatagt ggtgggcaga ggagaacaac agatcaatca ccattggcac   2160
aagtctggaa gcagcattgg caaagccttt acaaccaccc tcaaaggagc gcagagacta   2220
gccgctctag gagacacagc ttgggacttt ggatcagttg gaggggtgtt cacctcagtt   2280
gggaaggctg tccatcaagt gttcggagga gcattccgct cactgttcgg aggcatgtcc   2340
tggataacgc aaggattgct gggggctctc ctgttgtgga tgggcatcaa tgctcgtgat   2400
aggtccatag ctctcacgtt tctcgcagtt ggaggagttc tgctcttcct ctccgtgaac   2460
gtgcacgctg acactgggtg tgccatagac atcagccggc aagagctgag atgtggaagt   2520
ggagtgttca tacacaatga tgtggaggct tggatggacc ggtacaagta ttaccctgaa   2580
```

```
acgccacaag gcctagccaa gatcattcag aaagctcata aggaaggagt gtgcggtcta    2640
cgatcagttt ccagactgga gcatcaaatg tgggaagcag tgaaggacga gctgaacact    2700
cttttgaagg agaatggtgt ggaccttagt gtcgtggttg agaaacagga gggaatgtac    2760
aagtcagcac ctaaacgcct caccgccacc acggaaaaat tggaaattgg ctggaaggcc    2820
tggggaaaga gtattttatt tgcaccagaa ctcgccaaca cacctttgt ggttgatggt    2880 ccggagacca aggaatgtcc gactcagaat cgcgcttgga atagcttaga agtggaggat    2940
tttggatttg gtctcaccag cactcggatg ttcctgaagg tcagagagag caacacaact    3000
gaatgtgact cgaagatcat tggaacggct gtcaagaaca acttggcgat ccacagtgac    3060
ctgtcctatt ggattgaaag caggctcaat gatacgtgga agcttgaaag gcagttctg    3120 ggtgaagtca aatcatgtac gtggcctgag acgcatacct tgtggggcga tggaatcctt    3180
gagagtgact tgataatacc agtcacactg gcgggaccac gaagcaatca caatcggaga    3240
cctgggtaca agacacaaaa ccagggccca tgggacgaag gccgggtaga gattgacttc    3300
gattactgcc caggaactac ggtcacccctg agtgagagct gcggacaccg tggacctgcc    3360
actcgcacca ccacagagag cggaaagttg ataacagatt ggtgctgcag gagctgcacc    3420
ttaccaccac tgcgctacca aactgacagc ggctgttggt atggtatgga gatcagacca    3480
cagagacatg atgaaaagac cctcgtgcag tcacaagtga atgcttataa tgctgatatg    3540
attgaccctt ttcagttggg ccttctggtc gtgttcttgg ccacccagga ggtccttcgc    3600
aagaggtgga cagccaagat cagcatgcca gctatactga ttgctctgct agtcctggtg    3660
tttgggggca ttacttacac tgatgtgtta cgctatgtca tcttggtggg ggcagctttc    3720
gcagaatcta attcgggagg agacgtggta cacttggcgc tcatggcgac cttcaagata    3780
caaccagtgt ttatggtggc atcgtttctc aaagcgagat ggaccaacca ggagaacatt    3840
ttgttgatgt tggcggctgt ttctctttcaa atggcttatc acgatgcccg ccaaattctg    3900
ctctgggaga tccctgatgt gttgaattca ctggcggtag cttggatgat actgagagcc    3960
ataacattca caacgacatc aaacgtggtt gttccgctgc tagccctgct aacacccggg    4020
ctgagatgct tgaatctgga tgtgtacagg atactgctgt tgatggtcgg aataggcagc    4080
ttgatcaggg agaagaggag tgcagctgca aaaagaaag gagcaagtct gctatgcttg    4140
gctctagcct caacaggact tttcaacccc atgatccttg ctgctggact gattgcatgt    4200
gatcccaacc gtaaacgcgg atggcccgca actgaagtga tgcagctgt cggcctaatg    4260 tttgccatcg tcggagggct ggcagagctt gacattgact ccatgccat tccaatgact    4320 atcgcggggc tcatgtttgc tgcttttcgtg atttctggga aatcaacaga tatgtggatt    4380
gagagaacgg cggacatttc ctgggaaagt gatgcagaaa ttacaggctc gagcgaaaga    4440
gttgatgtgc ggcttgatga tgatggaaac ttccagctca tgaatgatcc aggagcacct    4500
tggaagatat ggatgctcag aatggtctgt ctcgcgatta gtgcgtacac cccctgggca    4560
atcttgccct cagtagttgg attttggata actctccaat acacaaagag aggaggcgtg    4620
ttgtgggaca ctccctcacc aaaggagtac aaaaagggg acacgaccac cggcgtctac    4680
aggatcatga ctcgtgggct gctcggcagt tatcaagcag gagcgggcgt gatggttgaa    4740
ggtgttttcc acaccctttg gcatacaaca aaaggagccg ctttgatgag cggagagggc    4800
cgcctggacc catactgggg cagtgtcaag gaggatcgac tttgttacgg aggaccctgg    4860
aaattgcagc acaagtggaa cgggcaggat gaggtgcaga tgattgtggt ggaacctggc    4920
aagaacgtta agaacgtcca gacgaaacca ggggtgttca aaacacctga aggagaaatc    4980
```

```
ggggccgtga ctttggactt ccccactgga acatcaggct caccaatagt ggacaaaaac    5040
ggtgatgtga ttgggcttta tggcaatgga gtcataatgc ccaacggctc atacataagc    5100
gcgatagtgc agggtgaaag gatggatgag ccaatcccag ccggattcga acctgagatg    5160
ctgaggaaaa aacagatcac tgtactggat ctccatcccg gcgccggtaa aacaaggagg    5220
attctgccac agatcatcaa agaggccata aacagaagac tgagaacagc cgtgctagca    5280
ccaaccaggg ttgtggctgc tgagatggct gaagcactga gaggactgcc catccggtac    5340
cagacatccg cagtgcccag agaacataat ggaaatgaga ttgttgatgt catgtgtcat    5400
gctaccctca cccacaggct gatgtctcct cacagggtgc cgaactacaa cctgttcgtg    5460
atggatgagg ctcatttcac cgacccagct agcattgcag caagaggtta catttccaca    5520
aaggtcgagc tagggaggc ggcggcaata ttcatgacga ccaccccacc aggcacttca    5580
gatccattcc cagagtccaa ttcaccaatt tccgacttac agactgagat cccggatcga    5640
gcttggaact ctggatacga atggatcaca gaatacaccg gaagacggt ttggtttgtg    5700
cctagtgtca agatggggaa tgagattgcc ctttgcctac aacgtgctgg aaagaaagta    5760
gtccaattga acgaaaagtc gtacgagacg gagtacccaa aatgtaagaa cgatgattgg    5820
gactttgtta tcacaacaga catatctgaa atggggcta acttcaaggc gagcagggtg    5880
attgacagcc ggaagagtgt gaaaccaacc atcataacag aaggagaagg gagagtgatc    5940
ctgggagaac catctgcagt gacagcagct agtgccgccc agagacgtgg acgtatcggt    6000
agaaatccgt cgcaagttgg tgatgagtac tgttatgggg ggcacacgaa tgaagacgac    6060
tcgaacttcg cccattggac tgaggcacga atcatgctgg acaacatcaa catgccaaac    6120
ggactgatcg ctcaattcta ccaaccagag cgtgagaagg tatataccat ggatgggaa    6180
taccggctca gaggagaaga gagaaaaaac tttctggaac tgttgaggac tgcagatctg    6240
ccagtttggc tggcttacaa ggttgcagcg gctggagtgt cataccacga ccggaggtgg    6300
tgctttgatg gtcctaggac aaacacaatt ttagaagaca acaacgaagt ggaagtcatc    6360
acgaagcttg gtgaaaggaa gattctgagg ccgcgctgga ttgacgccag ggtgtactcg    6420
gatcaccagg cactaaaggc gttcaaggac ttcgcctcgg gaaaacgttc tcagataggg    6480
ctcattgagg ttctgggaaa gatgcctgag cacttcatgg ggaagacatg ggaagcactt    6540
gacaccatgt acgttgtggc cactgcagag aaaggaggaa gagctcacag aatggccctg    6600
gaggaactgc cagatgctct tcagacaatt gccttgattg ccttattgag tgtgatgacc    6660
atgggagtat tcttcctcct catgcagcgg aagggcattg gaaagatagg tttgggaggc    6720
gctgtcttgg gagtcgcgac cttttttctgt tggatggctg aagttccagg aacgaagatc    6780
gccggaatgt tgctgctctc ccttctcttg atgattgtgc taattcctga ccagagaag    6840
caacgttcgc agacagacaa ccagctagcc gtgttcctga tttgtgtcat gaccccttgtg    6900
agcgcagtgg cagccaacga gatgggttgg ctagataaga ccaagagtga cataagcagt    6960
ttgtttgggc aaagaattga ggtcaaggag aatttcagca tgggagagtt tcttctggac    7020
ttgaggccgg caacagcctg gtcactgtac gctgtgacaa cagcggtcct cactccactg    7080
ctaaagcatt tgatcacgtc agattacatc aacacctcat tgacctcaat aaacgttcag    7140
gcaagtgcac tattcacact cgcgcgagc ttccccttcg tcgatgttgg agtgtcggct    7200
ctcctgctag cagccggatg ctgggacaa gtcaccctca ccgttacggt aacagcggca    7260
acactccttt tttgccacta tgcctacatg gttcccggtt ggcaagctga ggcaatgcgc    7320
tcagcccagc ggcggacagc ggccggaatc atgaagaacg ctgtagtgga tggcatcgtg    7380
```

```
gccacggacg tcccagaatt agagcgcacc acacccatca tgcagaagaa agttggacag    7440
atcatgctga tcttggtgtc tctagctgca gtagtagtga acccgtctgt gaagacagta    7500
cgagaagccg gaattttgat cacggccgca gcggtgacgc tttgggagaa tggagcaagc    7560
tctgtttgga acgcaacaac tgccatcgga ctctgccaca tcatgcgtgg gggttggttg    7620
tcatgtctat ccataacatg gacactcata agaacatgg aaaaaccagg actaaaaga     7680 ggtgggcaa aaggacgcac cttgggagag gtttggaaag aaagactcaa ccagatgaca    7740
aaagaagagt tcactaggta ccgcaaagag gccatcatcg aagtcgatcg ctcagcggca    7800
aaacacgcca ggaaagaagg caatgtcact ggagggcatc cagtctctag ggcacagca    7860 aaactgagat ggctggtcga acggaggttt ctcgaaccgg tcggaaaagt gattgacctt    7920
ggatgtggaa gaggcggttg gtgttactat atggcaaccc aaaaaagagt ccaagaagtc    7980
agagggtaca caagggcgg tcccggacat gaagagcccc aactagtgca aagttatgga    8040
tggaacattg tcaccatgaa gagtggagtg gatgtgttct acagccttc tgagtgttgt    8100 gacaccctcc tttgtgacat cggagagtcc tcgtcaagtg ctgaggttga agagcatagg    8160
acgattcggg tccttgaaat ggttgaggac tggctgcacc gagggccaag ggaattttgc    8220
gtgaaggtgc tctgccccta catgccgaaa gtcatagaga agatggagct gctccaacgc    8280
cggtatgggg gggactggt cagaaacca ctctcacgga attccacgca cgagatgtat    8340
tgggtgagtc gagcttcagg caatgtggta cattcagtga atatgaccag ccaggtgctc    8400
ctaggaagaa tggaaaaaag gacctggaag ggacccaat acgaggaaga tgtaaacttg    8460
ggaagtggaa ccagggcggt gggaaaaccc ctgctcaact cagacaccag taaaatcaag    8520
aacaggattg aacgactcag gcgtgagtac agttcgacgt ggcaccacga tgagaaccac    8580
ccatatagaa cctggaacta tcacggcagt tatgatgtga agcccacagg ctccgccagt    8640
tcgctggtca atggagtggt caggctcctc tcaaaaccat gggacaccat cacgaatgtt    8700
accaccatgg ccatgactga cactactccc ttcgggcagc agcgagtgtt caaagagaag    8760
gtggacacga aagctcctga accgccagaa ggagtgaagt acgtgctcaa cgagaccacc    8820
aactggttgt gggcgttttt ggccagagaa aaacgtccca gaatgtgctc tcgagaggaa    8880
ttcataagaa aggtcaacag caatgcagct ttgggtgcca tgtttgaaga gcagaatcaa    8940
tggaggagcg ccagagaagc agttgaagat ccaaaatttt gggagatggt ggatgaggag    9000
cgcgaggcac atctgcgggg ggaatgtcac acttgcattt acaacatgat gggaaagaga    9060
gagaaaaaac ccggagagtt cggaaaggcc aagggaagca gagccatttg gttcatgtgg    9120
ctcggagctc gctttctgga gttcgaggct ctgggttttc tcaatgaaga ccactggctt    9180
ggaagaagaa actcaggagg aggtgtcgag gcttgggcc tccaaaaact gggttacatc    9240
ctgcgtgaag ttggcacccg gcctgggggc aagatctatg ctgatgacac agctggctgg    9300
gacacccgca tcacgagagc tgacttggaa aatgaagcta aggtgcttga gctgcttgat    9360
ggggaacatc ggcgtcttgc cagggccatc attgagctca cctatcgtca caaagttgtg    9420
aaagtgatgc gccggctgc tgatggaaga accgtcatgg atgttatctc cagagaagat    9480 cagagggga gtggacaagt tgtcacctac gccctaaaca cttcaccaa cctggccgtc    9540 cagctggtga ggatgatgga aggggaagga gtgattggcc cagatgatgt ggagaaactc    9600
acaaaaggga aaggacccaa agtcaggacc tggctgtttg agaatgggga agaaagactc    9660
agccgcatgg ctgtcagtgg agatgactgt gtggtaaagc ccctggacga tcgctttgcc    9720
acctcgctcc acttcctcaa tgctatgtca aaggttcgca agacatcca agagtggaaa    9780
```

-continued

```
ccgtcaactg gatggtatga ttggcagcag gttccatttt gctcaaacca tttcactgaa   9840
ttgatcatga agatggaag aacactggtg gttccatgcc gaggacagga tgaattggta   9900
ggcagagctc gcatatctcc aggggccgga tggaacgtcc gcgacactgc ttgtctggct  9960
aagtcttatg cccagatgtg gctgcttctg tacttccaca aagagacct gcggctcatg  10020 gccaacgcca tttgctccgc tgtccctgtg aattgggtcc ctaccggaag aaccacgtgg  10080
tccatccatg caggaggaga gtggatgaca acagaggaca tgttggaggt ctggaaccgt  10140
gtttggatag aggagaatga atggatggaa gacaaaaccc cagtggagaa atggagtgac  10200
gtcccatatt caggaaaacg agaggacatc tggtgtggca gcctgattgg cacaagagcc  10260
cgagccacgt gggcagaaaa catccaggtg gctatcaacc aagtcagagc aatcatcgga  10320
gatgagaagt atgtggatta catgagttca ctaaagagat atgaagacac aacttttggtt  10380 gaggacacag tactgtagat atttaatcaa ttgtaaatag acaatataag tatgcataaa  10440
agtgtagttt tatagtagta tttagtggtg ttagtgtaaa tagttaagaa aattttgagg  10500
agaaagtcag gccgggaagt tcccgccacc ggaagttgag tagacggtgc tgcctgcgac  10560
tcaaccccag gaggactggg tgaacaaagc cgcgaagtga tccatgtaag ccctcagaac  10620
cgtctcggaa ggaggacccc acatgttgta acttcaaagc ccaatgtcag accacgctac  10680
ggcgtgctac tctgcggaga gtgcagtctg cgatagtgcc ccaggaggac tgggttaaca  10740
aaggcaaacc aacgccccac gcggccctag ccccggtaat ggtgttaacc agggcgaaag  10800
gactagaggt tagaggagac cccgcggttt aaagtgcacg gcccagcctg gctgaagctg  10860
taggtcaggg gaaggactag aggttagtgg agaccccgtg ccacaaaaca ccacaacaaa  10920
acagcatatt gacacctggg atagactagg agatcttctg ctctgcacaa ccagccacac  10980
ggcacagtgc gccgacaatg gtggctggtg gtgcgagaac acaggatct              11029
```

<210> SEQ ID NO 2
<211> LENGTH: 20
<212> TYPE: DNA
<213> ORGANISM: West Nile virus

<400> SEQUENCE: 2
ctggatcgat ggagaggtgt                                               20

<210> SEQ ID NO 3
<211> LENGTH: 20
<212> TYPE: DNA
<213> ORGANISM: West Nile virus

<400> SEQUENCE: 3
tccggtcttt cctcctcttt                                               20

<210> SEQ ID NO 4
<211> LENGTH: 20
<212> TYPE: DNA
<213> ORGANISM: West Nile virus

<400> SEQUENCE: 4
ctaccgtcag cgatctctcc                                               20

<210> SEQ ID NO 5
<211> LENGTH: 20
<212> TYPE: DNA
<213> ORGANISM: West Nile virus -continued

```
<400> SEQUENCE: 5
ttcctttgcc aaatagtccg                                        20

<210> SEQ ID NO 6
<211> LENGTH: 20
<212> TYPE: DNA
<213> ORGANISM: West Nile virus

<400> SEQUENCE: 6
gacgtcgggt catttgaagt                                        20

<210> SEQ ID NO 7
<211> LENGTH: 20
<212> TYPE: DNA
<213> ORGANISM: West Nile virus

<400> SEQUENCE: 7
actgcaattc caacaccaca                                        20

<210> SEQ ID NO 8
<211> LENGTH: 20
<212> TYPE: DNA
<213> ORGANISM: West Nile virus

<400> SEQUENCE: 8
atgtcctgga taacgcaagg                                        20

<210> SEQ ID NO 9
<211> LENGTH: 20
<212> TYPE: DNA
<213> ORGANISM: West Nile virus

<400> SEQUENCE: 9
ctcctccaac tgcgagaaac                                        20

<210> SEQ ID NO 10
<211> LENGTH: 20
<212> TYPE: DNA
<213> ORGANISM: West Nile virus

<400> SEQUENCE: 10
atcgcgcttg gaatagctta                                        20

<210> SEQ ID NO 11
<211> LENGTH: 20
<212> TYPE: DNA
<213> ORGANISM: West Nile virus

<400> SEQUENCE: 11
gacagccgtt ccaatgatct                                        20

<210> SEQ ID NO 12
<211> LENGTH: 20
<212> TYPE: DNA
<213> ORGANISM: West Nile virus

<400> SEQUENCE: 12
aggccgggta gagattgact                                        20

<210> SEQ ID NO 13
<211> LENGTH: 20
<212> TYPE: DNA
<213> ORGANISM: West Nile virus
```

```
<400> SEQUENCE: 13
cctgcagcac caatctgtta                                              20

<210> SEQ ID NO 14
<211> LENGTH: 20
<212> TYPE: DNA
<213> ORGANISM: West Nile virus

<400> SEQUENCE: 14
cagtgtttat ggtggcatcg                                              20

<210> SEQ ID NO 15
<211> LENGTH: 20
<212> TYPE: DNA
<213> ORGANISM: West Nile virus

<400> SEQUENCE: 15
ggcatcgtga taagccattt                                              20

<210> SEQ ID NO 16
<211> LENGTH: 20
<212> TYPE: DNA
<213> ORGANISM: West Nile virus

<400> SEQUENCE: 16
tggcagagct tgacattgac                                              20

<210> SEQ ID NO 17
<211> LENGTH: 20
<212> TYPE: DNA
<213> ORGANISM: West Nile virus

<400> SEQUENCE: 17
gccgttctct caatccacat                                              20

<210> SEQ ID NO 18
<211> LENGTH: 20
<212> TYPE: DNA
<213> ORGANISM: West Nile virus

<400> SEQUENCE: 18
atactggggc agtgtcaagg                                              20

<210> SEQ ID NO 19
<211> LENGTH: 20
<212> TYPE: DNA
<213> ORGANISM: West Nile virus

<400> SEQUENCE: 19
taacgttctt gccaggttcc                                              20

<210> SEQ ID NO 20
<211> LENGTH: 20
<212> TYPE: DNA
<213> ORGANISM: West Nile virus

<400> SEQUENCE: 20
ggctgaagca ctgagaggac                                              20

<210> SEQ ID NO 21
<211> LENGTH: 20
<212> TYPE: DNA
<213> ORGANISM: West Nile virus
```

<400> SEQUENCE: 21
acaggttgta gttcggcacc                                          20

<210> SEQ ID NO 22
<211> LENGTH: 20
<212> TYPE: DNA
<213> ORGANISM: West Nile virus

<400> SEQUENCE: 22
ccaggcactt cagatccatt                                          20

<210> SEQ ID NO 23
<211> LENGTH: 20
<212> TYPE: DNA
<213> ORGANISM: West Nile virus

<400> SEQUENCE: 23
ctaggcacaa accaaaccgt                                          20

<210> SEQ ID NO 24
<211> LENGTH: 20
<212> TYPE: DNA
<213> ORGANISM: West Nile virus

<400> SEQUENCE: 24
gattgacgcc agggtgtact                                          20

<210> SEQ ID NO 25
<211> LENGTH: 20
<212> TYPE: DNA
<213> ORGANISM: West Nile virus

<400> SEQUENCE: 25
atgtcttccc catgaagtgc                                          20

<210> SEQ ID NO 26
<211> LENGTH: 20
<212> TYPE: DNA
<213> ORGANISM: West Nile virus

<400> SEQUENCE: 26
cgcagacaga caaccagcta                                          20

<210> SEQ ID NO 27
<211> LENGTH: 20
<212> TYPE: DNA
<213> ORGANISM: West Nile virus

<400> SEQUENCE: 27
ttgacctcaa ttctttgccc                                          20

<210> SEQ ID NO 28
<211> LENGTH: 21
<212> TYPE: DNA
<213> ORGANISM: West Nile virus

<400> SEQUENCE: 28
gacgtcccag aattagagcg c                                        21

<210> SEQ ID NO 29
<211> LENGTH: 20
<212> TYPE: DNA
<213> ORGANISM: West Nile virus

<400> SEQUENCE: 29
tccggcttct cgtactgtct                    20

<210> SEQ ID NO 30
<211> LENGTH: 20
<212> TYPE: DNA
<213> ORGANISM: West Nile virus

<400> SEQUENCE: 30
ctctgtttgg aacgcaacaa                    20

<210> SEQ ID NO 31
<211> LENGTH: 20
<212> TYPE: DNA
<213> ORGANISM: West Nile virus

<400> SEQUENCE: 31
gccccacctc tttttagtcc                    20

<210> SEQ ID NO 32
<211> LENGTH: 20
<212> TYPE: DNA
<213> ORGANISM: West Nile virus

<400> SEQUENCE: 32
agtcgagctt caggcaatgt                    20

<210> SEQ ID NO 33
<211> LENGTH: 20
<212> TYPE: DNA
<213> ORGANISM: West Nile virus

<400> SEQUENCE: 33
tggtgtctga gttgagcagg                    20

<210> SEQ ID NO 34
<211> LENGTH: 20
<212> TYPE: DNA
<213> ORGANISM: West Nile virus

<400> SEQUENCE: 34
tgagtacagt tcgacgtggc                    20

<210> SEQ ID NO 35
<211> LENGTH: 20
<212> TYPE: DNA
<213> ORGANISM: West Nile virus

<400> SEQUENCE: 35
ttgagaggag cctgaccact                    20

<210> SEQ ID NO 36
<211> LENGTH: 20
<212> TYPE: DNA
<213> ORGANISM: West Nile virus

<400> SEQUENCE: 36
agctaaggtg cttgagctgc                    20

<210> SEQ ID NO 37
<211> LENGTH: 20
<212> TYPE: DNA
<213> ORGANISM: West Nile virus -continued

```
<400> SEQUENCE: 37
atgacggttc ttccatcagc                                          20

<210> SEQ ID NO 38
<211> LENGTH: 20
<212> TYPE: DNA
<213> ORGANISM: West Nile virus

<400> SEQUENCE: 38
acatccaaga gtggaaaccg                                          20

<210> SEQ ID NO 39
<211> LENGTH: 20
<212> TYPE: DNA
<213> ORGANISM: West Nile virus

<400> SEQUENCE: 39
cgagctctgc ctaccaattc                                          20

<210> SEQ ID NO 40
<211> LENGTH: 20
<212> TYPE: DNA
<213> ORGANISM: West Nile virus

<400> SEQUENCE: 40
gcaggaggag agtggatgac                                          20

<210> SEQ ID NO 41
<211> LENGTH: 20
<212> TYPE: DNA
<213> ORGANISM: West Nile virus

<400> SEQUENCE: 41
ttctccactg gggttttgtc                                          20

<210> SEQ ID NO 42
<211> LENGTH: 20
<212> TYPE: DNA
<213> ORGANISM: West Nile virus

<400> SEQUENCE: 42
gggttaacaa aggcaaacca                                          20

<210> SEQ ID NO 43
<211> LENGTH: 19
<212> TYPE: DNA
<213> ORGANISM: West Nile virus

<400> SEQUENCE: 43
ccctgaccta cagcttcag                                           19

<210> SEQ ID NO 44
<211> LENGTH: 20
<212> TYPE: DNA
<213> ORGANISM: West Nile virus

<400> SEQUENCE: 44
tagttcgcct gtgtgagctg                                          20

<210> SEQ ID NO 45
<211> LENGTH: 21
<212> TYPE: DNA
<213> ORGANISM: West Nile virus
```

```
<400> SEQUENCE: 45
ttttagcata ttgacagccc g                                              21

<210> SEQ ID NO 46
<211> LENGTH: 20
<212> TYPE: DNA
<213> ORGANISM: West Nile virus

<400> SEQUENCE: 46
ttgattggac tgaagagggc                                                20

<210> SEQ ID NO 47
<211> LENGTH: 20
<212> TYPE: DNA
<213> ORGANISM: West Nile virus

<400> SEQUENCE: 47
gcaattgctg tgaacctgaa                                                20

<210> SEQ ID NO 48
<211> LENGTH: 20
<212> TYPE: DNA
<213> ORGANISM: West Nile virus

<400> SEQUENCE: 48
gctgaagctg taggtcaggg                                                20

<210> SEQ ID NO 49
<211> LENGTH: 20
<212> TYPE: DNA
<213> ORGANISM: West Nile virus

<400> SEQUENCE: 49
ctggttgtgc agagcagaag                                                20

<210> SEQ ID NO 50
<211> LENGTH: 20
<212> TYPE: DNA
<213> ORGANISM: West Nile virus

<400> SEQUENCE: 50
ggagagtgca gtctgcgata                                                20

<210> SEQ ID NO 51
<211> LENGTH: 21
<212> TYPE: DNA
<213> ORGANISM: West Nile virus

<400> SEQUENCE: 51
gtctcctcta acctctagtc c                                              21

<210> SEQ ID NO 52
<211> LENGTH: 20
<212> TYPE: DNA
<213> ORGANISM: West Nile virus

<400> SEQUENCE: 52
gccaccggaa gttgagtaga                                                20

<210> SEQ ID NO 53
<211> LENGTH: 21
<212> TYPE: DNA
<213> ORGANISM: West Nile virus
```

```
<400> SEQUENCE: 53
gagacggttc tgagggctta c                                    21

<210> SEQ ID NO 54
<211> LENGTH: 30
<212> TYPE: DNA
<213> ORGANISM: West Nile virus

<400> SEQUENCE: 54
tggatttggt ctcaccagca ctcggatgtt                           30

<210> SEQ ID NO 55
<211> LENGTH: 30
<212> TYPE: DNA
<213> ORGANISM: West Nile virus

<400> SEQUENCE: 55
acatccgcag tgcccagaga acataatgga                           30

<210> SEQ ID NO 56
<211> LENGTH: 30
<212> TYPE: DNA
<213> ORGANISM: West Nile virus

<400> SEQUENCE: 56
acgggttcac tactactgca tctagagaca                           30

<210> SEQ ID NO 57
<211> LENGTH: 31
<212> TYPE: DNA
<213> ORGANISM: West Nile virus

<400> SEQUENCE: 57
ccggtaatgg tgttaaacca gggcgaaagg a                         31

<210> SEQ ID NO 58
<211> LENGTH: 30
<212> TYPE: DNA
<213> ORGANISM: West Nile virus

<400> SEQUENCE: 58
caggaggact gggttaacaa aggcaaacca                           30

<210> SEQ ID NO 59
<211> LENGTH: 30
<212> TYPE: DNA
<213> ORGANISM: West Nile virus

<400> SEQUENCE: 59
atcacttcgc ggctttgttc acccagtcct                           30
```